US010961542B2

(12) United States Patent
Dantas de Almeida et al.

(10) Patent No.: US 10,961,542 B2
(45) Date of Patent: Mar. 30, 2021

(54) COMPOSITIONS AND METHODS CONTAINING A CONSTITUTIVE PROMOTER TO MODIFY THE EXPRESSION OF GENES OF INTEREST IN PLANTS

(71) Applicants: EMPRESA BRASILEIRA DE PESQUISA AGROPECUÁRIA—EMBRAPA, Brasília (BR); FUNDAÇÃO UNIVERSIDADE DE BRASILIA—FUB—UNB, Brasília (BR)

(72) Inventors: Juliana Dantas de Almeida, Brasília (BR); Leila Maria Gomes Barros, Brasília (BR); Renata Henrique Santana, Brasília (BR); Ricardo Vilela Abdelnoor, Londrina (BR); Felipe Rodrigues da Silva, Brasília (BR)

(73) Assignees: EMPRESA BRASILEIRA DE PESQUISA AGROPECUÁRIA—EMBRAPA, Brasília (BR); FUNDACAO UNIVERSIDADE DE BRASILIA, Brasília (BR)

( * ) Notice: Subject to any disclaimer, the term of this patent is extended or adjusted under 35 U.S.C. 154(b) by 37 days.

(21) Appl. No.: 14/778,190

(22) PCT Filed: Mar. 18, 2014

(86) PCT No.: PCT/BR2014/000083
§ 371 (c)(1),
(2) Date: Sep. 18, 2015

(87) PCT Pub. No.: WO2014/146182
PCT Pub. Date: Sep. 25, 2014

(65) Prior Publication Data
US 2016/0272982 A1    Sep. 22, 2016

(30) Foreign Application Priority Data
Mar. 18, 2013    (BR) ............................ 102013007620

(51) Int. Cl.
*C12N 15/82*    (2006.01)

(52) U.S. Cl.
CPC ..... *C12N 15/8216* (2013.01); *C12N 15/8225* (2013.01); *C12N 15/8227* (2013.01); *C12N 15/8234* (2013.01); *C12N 15/8241* (2013.01)

(58) Field of Classification Search
None
See application file for complete search history.

(56) References Cited

U.S. PATENT DOCUMENTS

2007/0192897 A1* 8/2007 Hu ..................... C07K 14/415
                                                                800/278

OTHER PUBLICATIONS

Kuhlemeier et al. Genes Dev 1:247-55 (1987).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Potenza et al., In Vitro Cell Dev Biol Plant 40:1-22 (2004).*
Saha et al., In Silico Biol 7(1):7-19 (2007).*
Dolferus et al. (1994) Plant Physiol 105:1075-87.*
USPTO Written Description Training Materials (2008).*
Ryden & Beemon (1989) Mol Cell Biol 9(3):1155-64.*
Saha et al. (2007) In Silico Biol 7(1):7-19.*
Donald & Cashmore(1990) EMBO J 9:1717-26.*
Kim et al. (1994) Plant Mol Biol 24:105-17.*
International Preliminary Report on Patentability dated Sep. 22, 2015 issued in Application No. PCT/BR2014/000083.

* cited by examiner

*Primary Examiner* — Russell T Boggs
(74) *Attorney, Agent, or Firm* — Sughrue Mion, PLLC

(57) ABSTRACT

The present invention relates to a new promoter of the expression of genes in plants. More specifically, the invention relates to regulatory sequences of polynucleotides that are isolated from soy plants and can initiate and activate polynucleotide transcription, and to the use of these regulatory sequences to modify the transcription of endogenous and/or heterologous polynucleotides and to produce polypeptides. The invention further describes DNA constructs that contain the promoter of the gene of the supposed flavonol-sulfotransferase protein in soy plants, which promoter is functionally linked to a heterologous and/or endogenous gene. Moreover, the invention relates to the use of these constructs in the form of expression cassettes, expression vectors, recombinant vectors and in plants, plant cells or transgenic protoplasts. The invention also describes a method using such constructs that contain the promoter of the gene of the putative flavonol-sulfotransferase protein of soy plants for the production of transgenic plants, plant cells or protoplasts.

19 Claims, 10 Drawing Sheets

Specification includes a Sequence Listing.

SEQUENCE LISTING

```
<160> NUMBER OF SEQ ID NOS: 8

<210> SEQ ID NO 1
<211> LENGTH: 509
<212> TYPE: DNA
<213> ORGANISM: Glycine max

<400> SEQUENCE: 1
ggattggagt tgcttacttg aattttaaaa ttgaatttat ttcctctatt acattatagt      60
cttgtatttt tttacttaat ttatataatt gtgtttttca tgatttgtag ctaatatata     120
tcttttagtt attaatcaaa ttgaatatat taattttaaa ttataattta attttaattt     180
ttatattcgc ctcttaaaaa aggtttagtt cttccttagt cgatgatgat gatttctttt     240
aatttttcac aatgaaataa tttgtgcgct cgaaacagaa agaaagcttt gagtcgtcca     300
tcgctttcat ccagtgtttg atttgtcggt agcatgattc ctgcatgtgt tatattatgt     360
gtaccaaata attatcatat tctcataaaa aaaataatac cgcattcttt acttctactt     420
gtaccataaa tatagtgcta taaataacat atctttgtga tcaaaattct catgccaatc     480
agtaccagag atcgaccatt agcactcta                                       509

<210> SEQ ID NO 2
<211> LENGTH: 20
<212> TYPE: DNA
<213> ORGANISM: Glycine max

<400> SEQUENCE: 2
gtggccacaa ttccaaaatc                                                  20

<210> SEQ ID NO 3
<211> LENGTH: 20
<212> TYPE: DNA
<213> ORGANISM: Glycine max

<400> SEQUENCE: 3
ccaagttgga ccaaacccta                                                  20

<210> SEQ ID NO 4
<211> LENGTH: 23
<212> TYPE: DNA
<213> ORGANISM: Glycine max

<400> SEQUENCE: 4
caccggacaa tgcagggatt atg                                              23
```

```
<210> SEQ ID NO 5
<211> LENGTH: 24
<212> TYPE: DNA
<213> ORGANISM: Glycine max

<400> SEQUENCE: 5
cacctccatc tctttgttct ttac                                              24

<210> SEQ ID NO 6
<211> LENGTH: 24
<212> TYPE: DNA
<213> ORGANISM: Glycine max

<400> SEQUENCE: 6
caccggattg gagttgctta cttg                                              24

<210> SEQ ID NO 7
<211> LENGTH: 20
<212> TYPE: DNA
<213> ORGANISM: Glycine max

<400> SEQUENCE: 7
tagagtgcta atggtcgatc                                                   20

<210> SEQ ID NO 8
<211> LENGTH: 3257
<212> TYPE: DNA
<213> ORGANISM: Glycine max

<400> SEQUENCE: 8
ctttgaactg attattacct gggtgctgaa aaaaaatatt tttcatataa attctctaat        60
ttttctactt ttttctcatt ctgatcagca gatagagaca ttttttccagc tatttaaaaa      120 cattatttt tttatttctc ttgttttaat ttttttctta attttcttct tctttttatt        180
aatttgtttc ttttttcttg tttttttccct cgatatttca cgttgaatcc aaataaaat      240 tatacaggat cgctaaggta ttatccaagg taggttgttc aaaataaata aaggcaagaa      300
gcagcctaac aagaaaaaaa aaagtaaaac ataagaaaat tgttaataaa aaatggttat      360
atgttagaga tccgtagttc atagttggta aggcatatct ttgcatatcg tcggagaga       420 ttctttatta atttaatatg tttcagtctt actaagaatg gtggatattt atatactata     480 tttttttaata ataatttcaa ttatcatttt acgtataacg tgatatgcct ctaaacatgc    540
catattatac atatcagagt aattattgat cattttatat atctaaatga atgttatatt    600
attactaagc taatggaaaa aaaaaaaaac tgtgtctgca tttgacaaaa gagaaagatg     660
tacgtgagag attattagtt attatttata tagttaaaag attaatatac gtggtaaaaa    720
aaaaagataa atatgttaga gatgtgattg actaaaaaaa aataattaaa atatagtgat    780
gggtacgtgc tgaataacag ttaaaggata aattccttaa aaaaacaaaa gtggaaacca    840
aatgtgtgtc ccctctatta tatatatgta cggacaatgc agggattatg ttttttttaaa   900 attataaaat tatacacaca aatatgtata aaactataca agaagtatat atatatatat    960
atatatatat atatatatat atatatatat atatataatg ttttttactc ttttattact  1020
tgtagctctc caattttctt tttctttcca tctctttgtt ctttactaac gactataatt  1080
ttattacatt tcatactttc tttctctcct ctttctaact cttttattt tcttataatc   1140 tttccaacta ttttatcact aaagataaat acatctctca aaatctatac aaccatcatt  1200
tttcatattt ttgtaagatc tctccatttt ttctaaatat ttcataataa aaattaaaga  1260
```

-continued

```
aaaattattt catttgtgat tttttaaaac aggaaatgta ttgttcttat tactcatatt    1320
aaaaattaaa atttacttaa acaagatatt aggattggag ttgcttactt gaattttaaa    1380
attgaattta tttcctctat tacattatag tcttgtattt ttttacttaa tttatataat    1440 tgtgttttc atgatttgta gctaatatat atcttttagt tattaatcaa attgaatata    1500
ttaattttaa attataattt aattttaatt tttatattcg cctcttaaaa aaggtttagt    1560
tcttccttag tcgatgatga tgatttcttt taatttttca caatgaaata atttgtgcgc    1620
tcgaaacaga aagaaagctt tgagtcgtcc atcgctttca tccggtgttt gatctgtcgg    1680
tagcatgatt cctgcatgtg ttatattatg tgtaccaaat aattatcata ttctcataaa    1740
aaaatatcgc attctttact tctacttgta acacaaatat agtgctataa ataacatatc    1800
tttgtgatca aaattctcat gccaatcagt actagagatc gaccattagc actctaatgg    1860
ctccaacaaa tgtcacatgc ttcagagaag aaaatgaatc cgagaaaggg gaggaaataa    1920
caatagaaga agacaagcta agtcaagaat gtaaggagtt gatactctct cttcctaggg    1980
agagaggttg gagaacacgt tatatatatc tatttcaagg attttggtgc cagccattgg    2040
aaatccaagc aataatcact tttcagaagc acttccaagc taaagacagt gatgttattg    2100
tggccacaat tccaaaatca ggtaccactt ggctgaaagc tctcaccttt gccattgtca    2160
atcgccatac tcatagtatc actacatcaa tgtcatcaca tcctttgctt acttctaatc    2220
ctcatgaact tgtgcctttc atagaataca ccgtttatgg taatgcccct agccatgttc    2280
caaacctatc caacatgact gagccaagac ttttggtac acatattcca ttccatgcat    2340
tggccaagtc aatcaaggag tccaatagta gaataatttta tatatgtagg aacccacttg    2400
acacttttct gtctacttgg attttcctca acaaaattaa gccagaacat ttacctgaat    2460
ttgaactagg ggaagctttt gaaaagtatt gcaaaggaat aatagggttt ggtccaactt    2520
gggaccaaat gttgggttat tggaaggaga gtatagctag gcctagtaag gttttgttct    2580
tgaagtacga ggatcttaaa aaagatgtca attttcatgt gaaaagaata gcggagttct    2640
taggatggcc tttcacttcg gaggaagaag gtgatgggac tattgagagc ataatcaagc    2700
tatgcagctt cgagaagatg aaggaattgg aggcaaataa atctggaaca tttgctagga    2760
actttgagag aaagtacttg ttccgaaagg ctgaaatggg agattgggtg aactaccttt    2820
cccctgaaat gggtgaaaag ttatcgcaaa ttatggaaga aaagttaagt gggtcaggct    2880
tgtcatttta agtgtctcct tattttttgtt gatcgatcac tagctagtga tcatcatcta    2940
catcaagtgt ctaaataaga atcgtgcata tatgcaggtc atgatgtggc ctacaagtcc    3000
atgttcgttg tgattttccc ttttcccgtt tggatgattt ttcctactag tgcattgaag    3060
gtctcagtaa agttatttct atcatgcgtg ttttgtgttt aattaattaa gtgactcatt    3120
tgcttgtttt gtggtattat attatattat gacagataaa ctttggttct tgtatttttgg    3180 atatccttgg tgtcggggtg tatgaagatt aaggtttggt gtaagattaa aagtatcggt    3240
cgcggtaacg ttgtatg                                                   3257
```

COMPOSITIONS AND METHODS CONTAINING A CONSTITUTIVE PROMOTER TO MODIFY THE EXPRESSION OF GENES OF INTEREST IN PLANTS

FIELD OF THE INVENTION

This application is a National Stage of International Application No. PCT/BR2014/000083 filed Mar. 18, 2014, claiming priority based on Brazilian Patent Application No. 102013007620-1 filed Mar. 18, 2013, the contents of all of which are incorporated herein by reference in their entirety. The present invention relates to a new promoter of the expression of genes in plants. More specifically, the invention relates to regulatory sequences of polynucleotides that are isolated from soy plants and can initiate and activate polynucleotide transcription, and to the use of these regulatory sequences to modify the transcription of endogenous and/or heterologous polynucleotides and to produce polypeptides. The invention further describes DNA constructs that contain the promoter of the gene of the supposed flavonol-sulfotransferase protein in soy plants, which promoter is functionally linked to a heterologous and/or endogenous gene. Moreover, the invention relates to the use of these constructs in the form of expression cassettes, expression vectors, recombinant vectors and in plants, plant cells or transgenic protoplasts. The invention also describes a method using such constructs that contain the promoter of the gene of the supposed flavonol-sulfotransferase protein of soy plants for the production of transgenic plants, plant cells or protoplasts.

BACKGROUND OF THE INVENTION

In Brazil, the soybean has great economic importance, since the export of plant complex, consisting of beans, meal and oil, has the highest weight in the trade balance, and has become the commodity that generates most foreign exchange currently (Ministry of Development Industry and Foreign Trade, Trade balance—consolidated data, 2011. Available at: www.desenvolvimento.gov.br/arquivos/dwnl_1331125742.pdf. Accessed on Mar. 13, 2013). On the world stage, the country is the second largest producer of this commodity, according to the economic data of the harvest 2010/2011 (Conab, National Supply Company, 2013. Available at www.conab.gov.br/OlalaCMS/uploads/arquivos/12_09_06_09_18_33_boletim_graos_-_setembro_2012.pdf. Accessed on Mar. 13, 2013).

It is estimated that the production and consumption of soy increase as the world population grows, due to its importance both in food and feed as industrial and pharmaceutical applications (Hartman et al., Crops that feed the World 2. Soybean-worldwide production, use, and constraints caused by pathogens and pests. Food Security, v. 3, n. 1, p. 5-17, 2011). However, for the increase to be effective and sustainable, it is necessary to circumvent several factors that affect negatively production. Drought, flooding, freezing, availability of nutrients in the soil, salinity and photoperiod are some of the abiotic factors affecting soybean cultivation. Among the biotic factors are pests such as insects and microorganisms that cause diseases such as Asian soybean rust (*Phakopsora pachyrhizi*) and root infection by nematode (*Heterodera glycines*) (Hartman et al., Crops that feed the World 2. Soybean-worldwide production, use, and constraints caused by pathogens and pests. Food Security, v. 3, n. 1, p. 5-17, 2011).

The strategies that can be used to circumvent the losses by disease, pests and abiotic stresses are the use of pesticides, fertilizers, irrigation, or the development of resistant varieties of plants (Hartman et al., Crops that feed the World 2. Soybean-worldwide production, use, and constraints caused by pathogens and pests. Food Security, v. 3, n. 1, p. 5-17, 2011). However, agricultural inputs could threaten human health and the environment by contaminating groundwater, soil and accumulate in the end consumer product, ie the grains (Matson et al., Agricultural Intensification and Ecosystem Properties. Science, v. 277, n. 5325, p. 504-509, Jul. 25, 1997). Additionally, water availability and high costs may limit the irrigation system of culture, making it impractical in some cases (Hartman et al., Crops that feed the World 2. Soybean-worldwide production, use, and constraints caused by pathogens and pests. Food Security, v. 3, n. 1, p. 5-17, 2011). Genetic engineering is a powerful tool for the production of new soybean cultivars that can overcome the limitations of culture. Further, this technique contributes to increased productivity assisting the improvement, because it enhances the genetic basis of crops by introduction of features found in phylogenetically distant organisms to overcome genetic barriers (Singh e Hymowitz, Soybean genetic resources and crop improvement. Genome, v. 42, n. 4, p. 605-616, 1999).

Transgenics allows the inclusion of features that can benefit the plants and their products providing improvement of poorly adapted plants (Singh et al., Genetically-modified crops: Success, safety assessment, and public concern. Applied Microbiology and Biotechnology, v. 71, n. 5, p. 598-607, 2006). In several countries this technology is already being used to increase agricultural production, with Brazil being the country that has the second largest area planted with genetically-modified crops having nearly 27 million hectares of transgenic soybeans (Conab National Supply Company, 2013. Available at www.conab.gov.br/OlalaCMS/uploads/arquivos/12_09_06_09_18_33_boletim_graos_-_setembro_2012.pdf. Accessed on Mar. 13, 2013). Of the soybean cultivars approved for planting in Brazil, Roundup Ready, Cultivance and the Liberty Link™ feature tolerance to herbicides while the cultivar Intacta RR2 PRO, besides being herbicide tolerant produces the insecticidal protein CrylA (CTNBIO, National Biosafety Commission, 2013. Available at: www.ctnbio.gov.br/upd_blob/0001/1736.pdf. Accessed on Mar. 13, 2013). The development of research in the genomics area and the recent sequencing of the soybean genome (Schmutz et al., Genome sequence of the palaeopolyploid soybean. Nature, v. 463, n. 7278, p. 178-183, 2010) have made the creation of new varieties faster and more directed, since the genome provides information on gene expression, metabolic pathways, the structure of genetic material, the development and evolution of organisms. It is thus possible by means of genetic engineering to envision increased soybean production without expanding the planted area, by manipulating metabolic pathways to increase photosynthetic efficiency, nitrogen fixation in their reserve tissues and influence the reproductive phase of the species (Ainsworth et al., Accelerating yield potential in soybean: potential targets for biotechnological improvement. Plant, Cell & Environment, v. 35, n. 1, p. 38-52, 2012).

Transgenesis is the insertion of one or more genes capable of imparting a desirable characteristic to the body. It is called the transgene nucleotide sequence containing a promoter region, a coding region and a terminator region inserted into a host genome (Visarada et al., Transgenic breeding: Perspectives and prospects. Crop Science, v. 49, n. 5, p.

1555-1563, 2009). Transgenes may come from similar bodies or phylogenetically distant from the host (Singh et al., Genetically-modified crops: Success, safety assessment, and public concern. Applied Microbiology and Biotechnology, v. 71, n. 5, p. 598-607, 2006). The two methods most used to insert genes into plants are biolistic, in which the plant is bombarded by particles of gold or tungsten covered by the DNA of interest; and *Agrobacterium* sp, a soil bacterium that is capable of transferring a segment of its DNA into plants via Ti plasmid (tumor inducing) (Singh et al., Genetically-modified crops: Success, safety assessment, and public concern. Applied Microbiology and Biotechnology, v. 71, n. 5, p. 598-607, 2006).

The regulation of transgene expression will be, for the most part, by the promoter, the part of the gene which controls the transcription step, the first to suffer the control of gene expression. The expression of the transgene, however, is not uniform in all plants generated under the same conditions as it is subject to other endogenous regulatory mechanisms of the plant. The choice of a suitable promoter to regulate transgene expression may reduce this expression variability and increase the efficiency of the technique (Cammue et al., Approaches to minimize variation of transgene expression in plants. Molecular Breeding, v. 16, n. 1, p. 79-91, 2005).

While providing many benefits for agriculture to increase productivity, reduce pesticide use and costs, the cultivation of genetically-modified organisms also raises questions about ecological and toxicological safety (Singh et al., Genetically-modified crops: Success, safety assessment, and public concern. Applied Microbiology and Biotechnology, v. 71, n. 5, p. 598-607, 2006). One measure that can be used to reduce concerns about bio-GM plants is the use of promoters, regulatory sequences upstream (upstream) of the coding region responsible for the precise control of the transgenes, or promoters limit expression, that is, promoters that limit the expression thereof to a certain organ and/or period (Potenza et al., Targeting transgene expression in research, agricultural, and environmental applications: Promoters used in plant transformation. In Vitro Cellular & Developmental Biology—Plant, v. 40, n. 1, p. 1-22, 2004).

Currently, several isolated promoters are used to regulate transgenes in transformed plants: constitutive promoters, organ/tissue/cell-specific, inducible and synthetic promoters. The choice of the promoter to be used depends on the ultimate goal of transformation, be it to study gene expression and plant development, or commercial use (Potenza et al., 2004 Targeting transgene expression in research, agricultural, and environmental applications: Promoters used in plant transformation. In Vitro Cellular & Developmental Biology—Plant, v. 40, n. 1, p. 1-22, 2004).

There are two basic types of promoters, inducible and constitutive. An inducible promoter is a promoter capable of activating (directly or indirectly) the transcription of one or more DNA sequences or genes in response to a particular inducer. In the absence of such inducer the DNA sequences or genes will not be transcribed. The inducer can be a chemical component (described, for example, in the patent document WO9519443) a stress of physiological origin (as in the case of injury, which is described for example in patent document U.S. Pat. No. 6,677,505), or an endogenous compound generated in response to changes in plant development.

There are several tissue-specific promoters described for plants, such as seed specific expression (WO8903887), tuber (as mentioned in patent application US20030175783, Keil et al., 1989 EMBO J. 8: 1323:1330), leaves (as mentioned in patent application US20030175783, Hudspeth et al., 1989 Plant Mol Biol 12:579-589), fruit (Edwards and Coruzzi (1990) Annu. Rev. Genet. 24, 275-303 and U.S. Pat. No. 5,753,475), stem (as mentioned in patent application US20030175783, Keller et al., 1988 EMBO J. 7: 3625-3633), vascular tissues (as mentioned in patent application US20030175783, Peleman et al., 1989 Gene 84: 359-369 and SchmUlling et al. (1989) Plant Cell 1, 665-670), root (US20060143735 and as mentioned in patent application US20030175783, Keller et al., 1989 Genes Devel. 3:1639-1646), stamens (WO8910396, WO9213956), dehiscence zone specific promotors (WO9713865) and meristem (Ito et al. (1994) Plant Molecular Biology, 24, 863-878).

Constitutive promoters, in turn, are capable of promoting the expression of DNA sequences throughout plant development without spatial constraints. Accordingly, this expression occurs in a wide variety of cells and tissues of the plant. Nevertheless, the term "constitutive" does not mean that the sequence is expressed at the same levels in all plant cells.

With the recombination techniques, it is possible to enable the location of the start of transcription of a nucleotide sequence of interest, such as a heterologous sequence or not naturally occurring in a plant host cell.

Promoters which lead to constitutive expression of genes controlled by them can be used, for example, to select transformed plant cells, the expression of a selection marker gene in transgenic plants, the generation of antibiotic resistant plant cells or for generating plants that are herbicide-tolerant, and resistant to insects and pathogens, since the products of genes controlled by these are present in all parts of the plant. Exogenous genes of agronomic or medicinal importance, or other may be expressed in a variety of plants, for example for the generation of heterologous recombinant proteins and of plants containing mammalian polypeptides. The amount of the levels of spatial and temporal expression of endogenous plant genes, may also be advantageously modified with the aid of constitutively active promoters.

The first promoters used in the expression of genes in plants are viral or bacterial origin, in this case, bacteria of the *Agrobacterium* genus. Both systems have advantages in the case of heterologous expression in plants, because this principle is the basis of their infection mechanism. Many of these promoters have been widely used in the production of genetically-modified plants expressing proteins of interest.

In addition to the promoters derived from T-DNA of *Agrobacterium*, such as mannopine responsible for the synthesis of (mas), octopine synthase (ocs) and nopaline (in), there are promoters derived from viruses, among which the most widely used is the CaMV35S corresponding to the fragment of the 35S promoter of cauliflower mosaic virus. This same promoter had its regulatory region sequence doubled and fused to a sequence "enhancer" of the alfalfa mosaic virus, generating a recombinant plant promoter very efficient in inducing the expression of coding sequences associated with it.

Other constitutive promoters of viral origin include, for example, the promoter of Figwort mosaic virus (PI1101063-0), Badnavirus which infects the Australian banana (U.S. Pat. No. 6,391,639) and the promoter from the sugarcane bacilliform virus (U.S. Pat. No. 6,489,462). However, viral and *Agrobacterium* promoters have problems and may be particularly unstable and prone to horizontal gene transfer and gene recombination relative to its regulatory capacity, highlighting the importance of search of plant promoters.

The intrinsic constitutive plant promoters are, for example, the alpha tubulin promoter of coffee (U.S. Pat. No. 6,441,273), the promoter of the protein synthase trehalose- 6-phosphate *A. thaliana* (US20020115850), promoters of 2-actin, enolase, Gos-2 and L41 of corn (U.S. Pat. No. 6,670,467), V-ATPase promoter of *Beta vulgaris* (PI0013537-2), *Brassica* hsp80 promoter (PI9300296-3).

To express the selection gene and the resistance gene, it is desirable to have promoters available having a strong and uniform constitutive activity, if possible, in all plant tissues or cell types which, moreover, exhibit even greater activity or are not repressed under conditions of stress.

Even if the aforementioned promoters have been characterized as constituent, spatial and temporal expression patterns differ, making them unsuitable for certain applications. Therefore, it is necessary to explore and study other plant promoters. Furthermore, for certain applications in the production of genetically-modified plants, high levels of expression are desirable, thus increasing levels of the protein product of interest. High protein expression levels assist in generating plants exhibiting commercially important phenotypical properties, such as resistance to insect pests and diseases, tolerance to abiotic stress (e.g. drought, high temperatures, cold, light intensity, day-length, chemicals, etc.), improved quality (e.g., high fruit production, life cycle extension, uniformity of shape and color, high sugar content, high content of vitamin C and A, low acidity, etc.).

Promoters may be more effective if isolated from the same species of the transgenic plant to be generated. Studies show that the expression of β-glucuronidase (GUS), under control of the rice actin promoter (Act1) in transformed rice protoplasts was approximately 6 times higher than the expression under the control of the constitutive promoter of alcohol dehydrogenase (Adh1) of corn (US658701). Therefore, besides being able to the used as a constitutive promoter in various plant species, the promoter of the present invention has great advantages with respect to generation of transgenic soybean plants. Insect pest control in soybeans is a priority, as this crop is very important for Brazil, which is now the world's second largest producer, with an output of about 60 million tons.

For the control of these insect pests, the production of genetically-modified plants expressing proteins that confer resistance to the plant, has been used quite successfully. However, to achieve these plants, the control and directing of the expression of entomotoxic proteins are required. To obtain transgenic plants with adequate levels of proteins which confer insect resistance in plants, the choice of promoters which direct the expression is extremely important. However, there are few effective promoters for expression in soybean plants available on the market today.

The use of constitutive promoters often becomes necessary in the production of genetically-modified plants. The relevance of such use depends on the transgene function to be used in transformation or even the way that plant will be employed. In the case of transgenes conferring herbicide resistance, for example, it is desirable that expression be constitutive. In the case of more nutritious plant fodder through the influence of a transgene, the general expression is also desirable, since the cattle consumes the whole plant. Another application of constitutive promoters is in the transformation of a plant with more than one transgene. The promoter of the present invention has similar expression levels to that of the CaMV35S promoter, but was isolated from a plant genome, which may prevent gene silencing events and enhances availability of regulatory sequences for transformation events.

SUMMARY OF THE INVENTION

The invention relates to a polynucleotide sequence capable of modifying/inducing efficient expression of one or more genes of interest in plants, particularly the *Glycine* genus, as well as tools to obtain genetically-modified plants using this sequence and the use thereof. The usage possibilities of the invention are broad: prominently, the promoter used in methods for generating transgenics requiring high levels of constitutive expression such as: 1) transgenes, which confer herbicide resistance, 2) more nutritious fodder plants, 3) transformation of plants with multiple transgenes, 4) in case of incompatibility of a plant expression system with regulatory sequences of viral origin.

The polynucleotide according to the present invention has homology to the nucleotide sequence as shown in SEQ ID NO: 1, and 50% identity, preferably 60%, preferably 70%, preferably 80%, preferably 90%, more preferably 95% or higher.

In a first embodiment, the present invention provides a polynucleotide sequence which is substantially similar to SEQ ID NO: 1; a reverse sequence of SEQ ID NO: 1; probes and primers corresponding to SEQ ID NO: 1.

In another aspect, the invention provides chimeric genes comprising the polynucleotide of the present invention or alone, or in combination with one or more known polynucleotides, together with cells and organisms comprising these chimeric genes.

In a related aspect, the present invention provides recombinant vectors comprising, in the direction 5'-3', a polynucleotide promoter sequence of the present invention, a polynucleotide to be transcribed, and a gene termination sequence. The polynucleotide to be transcribed may comprise an open reading frame of a polynucleotide encoding a polypeptide of interest, or may be a region of non-coding or untranslated region, of a polynucleotide of interest. The open reading frame may be oriented in a "sense" or "antisense" direction. Preferably, the gene termination sequence is functional in a host plant. Preferably, the gene termination sequence is that of the gene of interest, but can be others described in the state of the art such as the nopaline synthase terminator of *A. tumefaciens*. The recombinant vector may further comprise a marker for identifying transformed cells.

In another aspect, the cells of transgenic plants comprising the expression cassette of the present invention are provided, together with organisms such as plants comprising such transgenic cells, and fruits, seeds and other products, derivatives, or progeny of these plants. Propagating material of inventive transgenic plants are included in the present invention.

In another aspect of the invention there is provided a method for modifying the expression of genes in an organism such as a plant, including the stable incorporation into the genome of the organism containing the recombinant vector of the present invention.

In another aspect of the invention a method is provided to produce a transformed organism such as a plant, and expressing a modified polypeptide. This method comprises transforming a plant cell with the expression cassette of the present invention to provide a transgenic cell under conditions conducive to regeneration and mature plant growth.

In yet another aspect of the invention there is provided a method for identifying a gene responsible for a desired function or phenotype. The method comprises: 1) transforming a plant cell containing a recombinant vector comprising a polynucleotide promoter sequence of the present invention operably linked to a polynucleotide to be tested, 2) culturing the plant cell under conditions conducive to regeneration and mature plant growth so as to provide a transgenic plant, and 3) comparing the phenotype of the transgenic plant with the phenotype of non-transformed plants, or wild type.

The above and additional aspects of the present invention and the manner of obtaining them will become apparent, and the invention will be better understood by reference in "Detailed Description of the Invention".

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
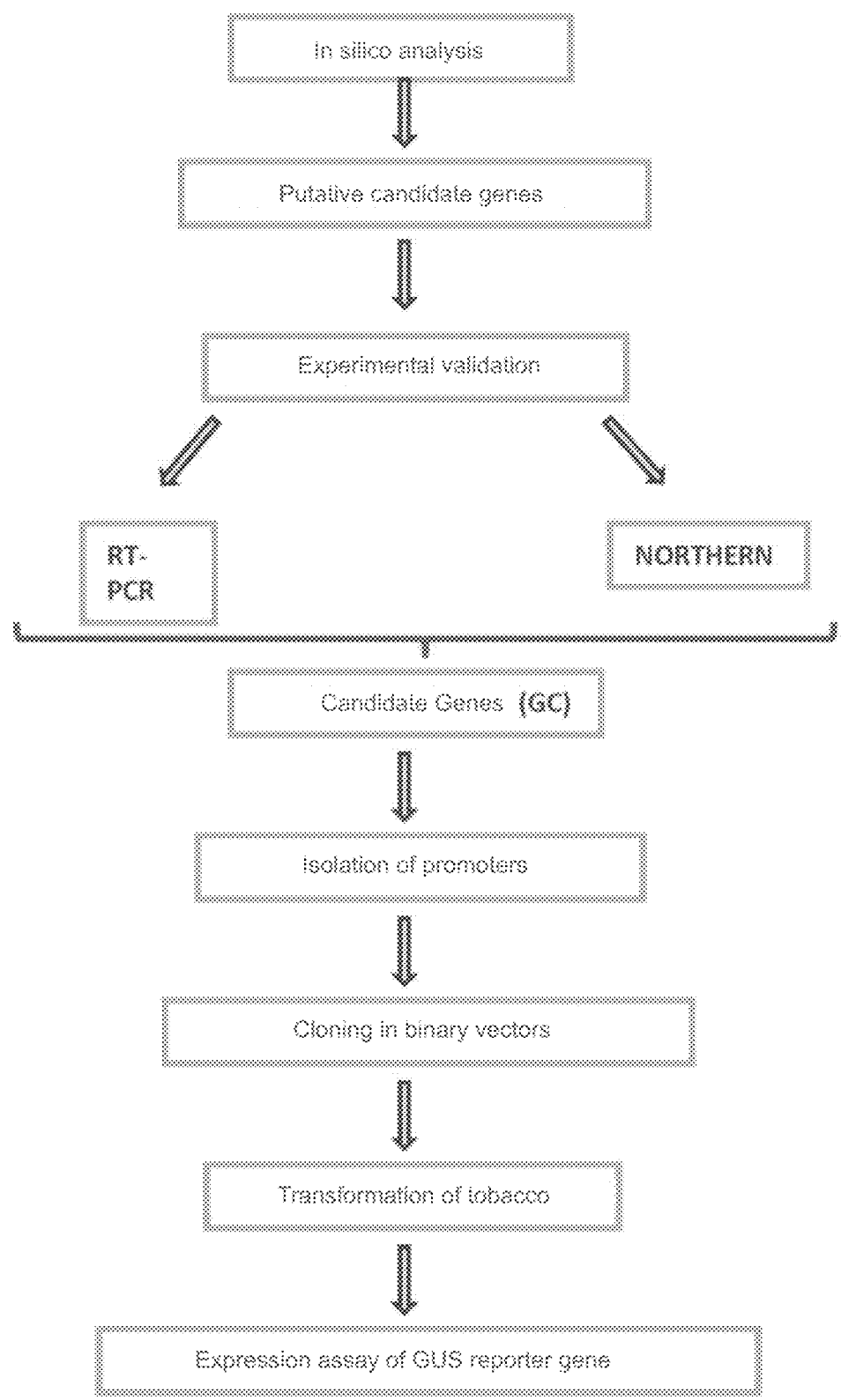
FIG. 1. Flow chart indicating the research steps involved in isolating the promoters.

The purpose of the present invention is to provide a method for modifying the expression, as well as an efficient promoter sequence for plants, preferably of the *Glycine* genus, so as to enable the production of genetically-modified varieties expressing genes of interest throughout the plant.

In the description that follows, a number of terms are used extensively. The following definitions are provided to facilitate understanding of the invention. In the context of this description, several terms will be used and so are explained in greater detail below:

A "chimeric gene" is a gene comprising a promoter and a coding region of different origins. In the case of the present invention, the chimeric gene comprises the polynucleotides of the invention linked to coding regions of endogenous and/or exogenous genes.

A "consensus sequence" is an artificial sequence in which the base of each position represents the base most frequently found in the current sequence, comparing different alleles, genes or organisms.

The terms "promoter", "promoter region" or "promoter sequence" can be used interchangeably and meant to denote, according to the present invention, that portion of the DNA upstream of the coding region containing binding sites for RNA polymerase II to begin transcription of the DNA, thereby providing a control point for regulated gene transcription. In eukaryotes, initiation of transcription is dependent on binding to the promoter a group of proteins called transcription factors. These factors bind to promoter sequences recruiting the RNA polymerase, the enzyme that synthesizes the RNA from the coding region of the gene.

The promoter of genes transcribed by the RNA polymerase II (Pol II) is a key region that regulates the differential transcription of proteins that they encode. The gene-specific architecture of the promoter sequences makes it extremely difficult to plan the overall strategy to predict promoters. The regions flanking the promoter are particularly poorly described and little understood (Shahmuradov et al (2005) Nucleic Acids Research, 33(3):1069-076). These regions may contain dozens of short motifs (5-10 bases) that serve as recognition sites for proteins involved at the start of transcription, and specific regulation of gene expression. Each promoter has unique selection and arrangement of such elements generating a unique pattern of gene expression.

The binding site of general transcription factors can be divided into 3 parts. The proximal promoter, which is proximal sequence upstream of the gene that tends to contain the primary regulatory elements. This region of 200-300 bp is upstream of the core promoter and contains multiple transcription factor binding sites which are responsible for regulating the specific transcription. The Distal promoter, which is the distal sequence upstream of the gene that may contain the additional regulatory elements, usually with a weaker influence than that of the proximal promoter. The position is not very clear. It is known only that is upstream (but not as an enhancer or other regulatory region whose influence is independent of the position/orientation). The distal promoter distal also has binding sites for specific transcription factors (Smale, (2001) Genes Dev., 15:2503-2508). Finally, the core promoter.

As promoters are typically immediately adjacent to the gene in question, the position of the promoters is designated relative to the transcription start site where RNA transcription begins with a particular gene, that is, upstream positions are negative numbers, the countdown starting by −1, for example, the position −100 is 100 base pairs upstream.

The core promoter is the minimal promoter region able to initiate basal transcription. It contains the transcription start site (TSS) and typical extensions ranging from −60 to +40 relative to TSS. Approximately 30-50% of all known promoters contain one TATA box located 45-25 bp upstream of the TSS. The TATA-box is apparently the best preserved functional signal in eukaryotic promoters and in some cases may direct the precise beginning of transcription by Pol II, even in the absence of other controlling elements. Many highly expressed genes contain a strong TATA-box at their core promoter. However, in some large groups of genes, such as housekeeping and photosynthesis genes, the TATA-box region is often absent, and the corresponding promoters are cited as promoters without a TATA-box. In these promoters, the exact location of the transcription start point can be controlled by the sequence of the transcription initiation region of nucleotides (INR) or the downstream promoter element (DPE), which is usually observed 30 bp downstream of the TSS (Burke and Kadonaga (1997) Genes Dev 11:3020-3031; Smale, (1997) Biochim Biophys Acta 1351: 73-88). The region where it binds to RNA polymerase II called TATA BOX u consensus sequence TATAAA, located nucleotides 25 to 30 above the transcription start point (−25 to −30). The TATA-box region typically appears very close to the transcription start site (usually less than 50 bases). Many promoters contain other sequences, such as the CAT box region (−70 to −80), which has the consensus sequence CAAT or CCAAT and the GC box region (−110), which has the consensus sequence GGGCGG. Promoter regions CAT box and GC box appear to function as enhancers and transcription factor binding sites (Smale and Kadonaga, (2003) Annu See Biochem 72:449-479). A wide variety of algorithms have been developed to facilitate the detection of promoters in genomic sequences, and predicting promoters is a common element of many gene-prediction methods. The first comprehensive review of performance of many programs with the function of predicting promoters was presented by Fickett and Hatzigeorgiou, (1997) (Genome Res., 7:861-878). Although the small number of tested sequences (18 sequences) presented various problems (Ohler et al (1999) Bioinformatics., 15:362-369), the results showed that the tested programs can recognize approximately 50% of promoters with false positive rate of 1 to every 700-1000 bp (Pedersen et al (1999) Phytopathology, 87(1):96-100; Ohler and Niemann, (2001) Trends Genet 17:56-60). However, it is important to improve the efficiency of promoter prediction in unique sequences (due to the frequent lack of information on the sequences of orthologous genes).

"Expression" is the transcription or translation of a structural, endogenous or heterologous gene.

The term "gene" means a physical and functional unit of heredity, represented by a DNA segment encoding a functional protein or RNA molecule.

An "endogenous gene" is a gene itself of the cell or organism.

A "heterologous gene" is a gene isolated from a donor organism and recombinant in the transformed host organism. It is a gene that is not specific to the cell or organism.

A "reporter gene" is a coding unit whose product is easily tested, for example, genes CAT, GUS, GAL, GFP and LUC. The expression of a reporter gene can be used to test the function of a promoter linked to this reporter gene.

The term "propagule" as used herein means any part of a plant that may be used in reproduction or propagation, sexual or asexual including the seedlings.

"Sense" means that the polynucleotide sequence is in the same orientation 5'-3' with respect to the promoter.

"Antisense" means that the polynucleotide sequence is in reverse orientation relative to the promoter's 5'-3 orientation.

As used herein, the term "X-mer" in reference to a specific value "x" refers to a sequence comprising at least a specific number ("x") of residues of the polynucleotide identified as SEQ ID NO: 1. According to preferred embodiments, the value of x is preferably at least 20, more preferably at least 40, even more preferably at least 60 and most preferably at least 80. Thus, polynucleotides of the invention comprise a polynucleotide of 20 mers, 40 mers, 60 mers, 80 mers, 100 mers, 120 mers, 150 mers, 180 mers, 220 mers, 250 mers, 300 mers, 400 mers, 500 or 600 mers identified as SEQ ID NO: 1 and variants thereof.

The term "polynucleotide (s)", as used herein, means a single or double-stranded polymer of deoxyribonucleotide ribonucleotide or corresponding bases and includes DNA and RNA molecules, including hnRNA and mRNA molecules; filaments both "sense" and "antisense", and includes cDNA, genomic DNA and recombinant DNA, as well as wholly or partially synthesized polynucleotides. A hnRNA molecule contains introns and corresponds to a DNA molecule in a generally one to one manner. An mRNA molecule corresponds to an hnRNA and DNA molecule from which the introns have been excised. A polynucleotide may consist of an entire gene, or any portion thereof. The operable "antisense" polynucleotides may comprise a fragment of the corresponding polynucleotide, and the definition of "polynucleotide" therefore includes all such operable antisense fragments. Antisense polynucleotides and techniques involving antisense polynucleotides are well known in the art (Sambrook, J.; E. F. Fritsh and T. Maniatis—Molecular cloning A laboratory manual, $2^{nd}$ edition, Cold Spring Harbor Laboratory Press, 1989).

The polynucleotides described in the present invention are preferably about 80% pure, more preferably at least about 90% pure, more preferably at least about 99% pure.

The term "oligonucleotide" refers to a relatively short segment of a polynucleotide sequence, generally comprising between 6 and 60 nucleotides. These oligonucleotides can be used as probes or primers, where the probes can be used for use in hybridization tests and primers for use in DNA amplification by polymerase chain reaction.

The term "probe" as used herein, refers to an oligonucleotide, polynucleotide or nucleic acid, being RNA or DNA, whether occurring naturally as in a purified restriction enzyme digest or produced synthetically, which is capable of enchaining with or specifically hybridizing with a nucleic acid containing complementary sequences to the probe. A probe also can be single stranded or double stranded. The exact length of the probe will depend on many factors, including temperature, source of probe and use of the method. For example, depending on the complexity of the target sequence, the oligonucleotide probe typically contains 15-25 or more nucleotides, although it may contain fewer nucleotides. The probes herein are selected to be complementary to differentiate strands of a sequence of a particular nucleic acid. This means that the probe can be sufficiently complementary to be able to "specifically hybridize" or enchain with their respective target strands under a set of predetermined conditions. Therefore, the probe sequence need not reflect the exact complementary sequence of the target. For example, a nucleotide fragment may be attached to the non-complementary 5' end or 3' end of the probe, with the remainder of the probe sequence being complementary to the target strand. Alternatively, non-complementary bases or longer sequences can be interspersed into the probe if it has sufficient complementarity with the sequence of the target nucleic acid to enchain specifically with it.

The term "primer" as used herein refers to an oligonucleotide, either RNA or DNA, single-stranded or double-stranded, derivative of a biological system, generated by restriction enzyme digestion, or produced synthetically that when placed in a proper environment it is able to functionally act as an initiator of nucleic acid synthesis template dependent. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The 'primer' can vary in length depending on the particular conditions and requirements for application. For example, for diagnostic applications, the "primer" oligonucleotide typically has 15-25 or more nucleotides in length. The 'primer' should have sufficient complementarity to the desired template to prime the synthesis of extension of the desired product. This does not mean that the sequence of 'primer' should represent an exact complement of the desired mold. For example, a non-complementary nucleotide sequence may be linked to the 5' end of a complementary primer. Alternatively, non-complementary bases may be interspersed within the oligonucleotide sequence 'primer', since 'primer' has sufficient complementarity with the sequence of the desired template strand to functionally provide template-primer complex for synthesis of the extension product.

Probes and primers are described as corresponding to the polynucleotide of the present invention identified as SEQ ID NO or a variant thereof, if the oligonucleotide probe or primer or its complement, is contained within the sequence specified as SEQ ID NO: 1 or a variant thereof.

The term "oligonucleotide" is referred to herein as "primers" and "probes" of the present invention, and is defined as a nucleic acid molecule comprising two or more ribo or deoxyribonucleotide, preferably more than three. The exact size of the oligonucleotides will depend on many factors and the particular application and use of oligonucleotides. Preferred oligonucleotides comprise 15-50 consecutive base pairs complementary to SEQ ID NO: 1. The probes can be readily selected using procedures well described in the art (Sambrook et al "Molecular Cloning, a laboratory manual", CSHL Press, Cold Spring Harbor, N.Y., 1989), taking into account DNA-DNA hybridization constraints, recombination and melting temperatures, and the potential for formation of loops, and other factors that are known in the art.

The definition of the terms "complement" and "reverse complement" and "reverse sequence", as used here, is illustrated by the following example: For the 5'AGTGAAGT3 sequence ', the add-on is 3TCACTTCA5', the reverse complement is 3'ACTTCACT5' and reverse sequence is 5TGAAGTGA3'. As used herein, the term "variant" or "substantially similar" comprises amino acid sequences of nucleotide or different nucleotide sequences specifically identified, in which one or more nucleotides or amino acid residues is deleted, substituted or added. Variants may be allelic variants, naturally occurring or non-naturally occurring variants. Variants or substantially similar sequences refer to nucleic acid fragments may be characterized by the percent similarity of their sequences of nucleotides with the nucleotide sequences described herein (SEQ ID NO: 1), as determined by standard algorithms employed in the art. Preferred nucleic acid fragments are those whose nucleotide sequences have at least about 40 or 45% sequence identity, preferably about 50% or 55% sequence identity, more preferably about 60% or 65% identity sequence, more preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence. The percentage identity is determined by aligning the two sequences to be compared, determining the number of identical residues in the aligned portion, dividing that number by the total number of residues in the searched sequence, and multiplying the result by 100. This alignment can be done through software existing on the Internet, one is the BLASTN, which is available from the National Center for Biotechnology Information website/ NCBI (www.ncbi.nlm.nih.gov).

"Variants" or "homologous sequences" of polynucleotides or polypeptides, for purposes of the present invention, involve sequences having a percentage identity with the polynucleotide sequence or polypeptide described by the invention, at least (or at least about) 20.00% to 99.99% (inclusive). The aforementioned identity range must be taken as including, and written description provided and support for, any percentage fraction at intervals of 0.01% between 20.00% and up to and including 99.99%. These percentages are purely statistical and differences between two nucleic acid sequences can be distributed randomly and over the entire length of the sequence. Homologous sequences may, for example, display percentage identities of 20, 21, 22, 23, 24, 25, 26, 27, 28, 29, 30, 31, 32, 33, 34, 35, 36, 37, 38, 39 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 90, 91, 92, 93, 94, 95, 96 97, 98, or 99 percent with the sequences of the present invention. Typically, the percent identity is calculated with reference to the full-length, native and/or naturally occurring polynucleotide. The terms "identical" or "identity" percentage in the context of two or more polynucleotide or polypeptide sequences, refers to two or more sequences or subsequences that are the same or have a specified percentage of amino acid residues that are the same when compared and aligned for maximum correspondence in a comparison window, as measured using a sequence comparison algorithm or by manual alignment and visual inspection. In certain aspects of the invention, sequences homologous to SEQ ID NO: 1 have at least 70% sequence identity over the full length (or along the full length of a fragment of SEQ ID NO: 1). Homologous sequences of both proteins and nucleic acids can be assessed using any of a variety of sequence comparison algorithms and programs known in the art. Such algorithms and programs include, but are in no way limited to, TBLSTN, BLASP, FASTA, TFASTA, and CLUSTALW (Pearson and Lipman, 1988, Proc. Natl. Acad. Sci. USA 85(8):2444-2448; Altschul et al., 1990, J. Mol. Biol. 251(3): 403-410; Thompson et al., 1994, Nucleic Acids Res. 22(2): 4673-4680; Higgins et al., 1996, Methods Enzymol.266: 383-402; Altschul et al., 1990, J. Mol. Biol. 215(3):403-410; Altschul et al., 1993, Nature Genetics 3:266-272).

Sequence comparisons are typically conducted using the default settings provided by the seller, or by using the parameters given in the references identified above, which according to which, incorporated by reference in its entirety.

Sequence homology and sequence identity can also be determined by hybridization studies under high stringency hybridization, intermediate and/or low stringency hybridization. Various degrees of hybridization stringency can be employed. The more severe the conditions, the greater the required complementarity for the formation of duplex tapes. The stringency of the conditions can be controlled by temperature, probe concentration, probe length, ionic strength, time and the like. Preferably, hybridization is conducted under low, medium and high accuracy by known techniques as described, for example, in Keller G H, Manak M M [1987] DNA Probes, Stockton Press, New York, N.Y., pp. 169-170. The term "specifically hybridizing" refers to the association between two molecules of single-stranded nucleic acids having sufficiently complementary sequence to permit such hybridization under pre-determined conditions generally described in the prior art. In particular, the term refers to hybridization of an oligonucleotide with a substantially complementary sequence containing a DNA molecule or single-stranded RNA of the present invention. Suitable conditions necessary for performing the specific hybridization between nucleic acid molecules of single-stranded complementary varied are well described in the art.

Hybridization of immobilized DNA on Southern blots, for example, with specific gene probes labeled with 32P can be conducted by standard methods (Maniatis et al [1982] Molecular Cloning: A Laboratory Manual, Cold Spring Harbor Laboratory, New York). In general, hybridization and subsequent washes can be done under medium to high stringency to allow detection of target sequences with homology to the exemplified polynucleotide sequence. For genetic probes double-stranded DNA, hybridization can be performed during overnight at 20-25° C. below the melting temperature (Tm) of the DNA hybrid in 6×SSPE, 5×Denhardt's solution, 0.1% SDS, denatured DNA 0.1 mg/ml. The melting temperature is described by the following formula (Betlz et al [1983] Methods of Enzymoiogy, R. Wu, L Grossman and K. Moldave, Academic Press, New York 100. [Eds.]: 266-285).

$$Tm = 81.5° C. + 16.6 \log[Na+] + 0.41(\% G+C) - 0.61(\% \text{formamide}) - 600/\text{length of duplex in base pairs}.$$

Washes are typically carried out as follows:
(1) twice at ambient temperature for 15 minutes 1×SSPE, SDS 0.1% (intermediate stringency wash);
(2) Once at Tm−20° C. for 15 minutes in 0.2×SSPE, SDS 0.1% (intermediate stringency wash)

For oligonucleotide probes hybridization can be carried out overnight at 10-20° C. below the denaturation temperature (Tm) of the hybrid in 6×SSPE, 5×Denhardt's solution, SDS 0.1% and 0.1 mg/ml DNA denatured. Tm for the oligonucleotide probe can be determined by the following formula:

$$Tm (° C.) = 2(\text{number of pairs of } T/A \text{ bases}) + 4(\text{number of base pairs } G/C)$$

(Suggs et al. [1981] ICN-UCLA Symp. Dev. Biol. Using Purified Genes, D. D. Brown [ed.], Academic Press, New York, 23:683-693).

Washes can be performed as follows:
(1) twice at ambient temperature for 15 minutes 1×SSPE, SDS 0.1% (low stringency wash);
(2) once at the hybridization temperature for 15 minutes SSPE 1×, SDS 0.1% (intermediate stringency wash).

In general salts and temperature can be altered to modify the stringency. With a labeled DNA fragment>70 bases in length, the following conditions may be used.
Low: 1 or 2×SSPE, ambient temperature
Low: 1 or 2×SPPE, 42° C.
Intermediate: 1×SSPE 0.2 or 65° C.
High: 0.1×SSPE, 65° C.

By way of another non-limiting element, procedures using conditions of high stringency can be achieved in the following ways: Pre-hybridization of filters containing DNA is carried out for 8 h overnight at 65° C. in buffer composed of 6×SSC, Tris-HCl 50 mM (pH 7.5), 1 mM EDTA, 0.02% PVP, 0.02% Ficoll, 0.02% BSA, and 500 µg/ml denatured salmon sperm DNA. Filters are hybridized for 48 h at 65° C., at the preferred hybridization temperature, in prehybridization mixture containing 100 µg/ml denatured salmon sperm DNA and 5-20×106 cpm probe labeled with 32P. Alternatively, the hybridization step can be performed at 65° C. in the presence of SSC buffer, 1×SSC corresponding to 0.15M NaCl and 0.05 M sodium citrate. Subsequently, filter washes can be done at 37° C. for 1 h in a solution containing 2×SSC, 0.01% PVP, 0.01% Ficoll and 0.01% BSA, followed by a wash in 0.1×SSC at 50° C. for 45 minutes. Alternatively, filters can be washed in a solution containing 2×SSC and 0.1% SDS or 0.5×SSC and 0.1% SDS, or 0.1×SSC and SDS at 68° C. for 15 minute intervals. Following the washing steps the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, NY, pp. 9:47 to 9:57; and Ausubel et al., 1989, Current Protocols in Molecular Biology, Green Publishing Associates and Wiley Interscience, NY are incorporated herein in their entirety.

Another non-limiting example procedures using conditions of intermediate stringency are as follows: Filters containing DNA are prehybridized, and then hybridized at a temperature of 60° C. in the presence of 5×SSC buffer and labeled probe. Subsequently, filters washes are done in a solution containing 2×SSC at 50° C. and the hybridized probes are detectable by autoradiography. Other conditions of intermediate stringency which may be used are well known to those skilled in the art as cited in Sambrook et al, 1989, Molecular Cloning, A Laboratory Manual, Second Edition, Cold Spring Harbor Press, NY, pp 9:47 to 9:57.; and Ausubel et al., 1989, Current Protocols in Molecular Biology, Green Publishing Associates and Wiley Insterscience, NY are incorporated herein in their entirety.

Another embodiment of the invention comprises methods for expression of heterologous sequences in plants controlled by new promoter sequences. The term "heterologous nucleotide sequence" means a sequence that is not naturally found operably linked to the promoter sequence. While this nucleotide sequence is heterologous to the promoter sequence, it may be homologous or heterologous to the plant. "Operably linked" means the joining of two nucleotide sequences so that the coding sequence of each DNA fragment is in the correct reading frame.

For the gene of interest to be expressed in a plant, however, the polynucleotide containing the gene sequence must be operatively linked to the polynucleotide containing the promoter sequence provided by the invention, configuring the expression cassette. The techniques used to construct an expression cassette are routine and known to skilled in the art (Sambrook et al., 1989, Molecular Cloning, A Laboratory Manual, Second Edition, Cold Spring Harbor Press, NY).

Another embodiment of the invention therefore comprises expression cassettes containing the polynucleotides, gene expression promoters in plants provided by the invention.

The expression cassettes can be assembled, or subsequently inserted into vectors which allow the production of copies of the cassette by propagating cells transformed with said vectors, such as *E. coli*, in culture medium. Such vectors should contain a functional origin of replication for the cell type being used and a marker gene, preferably resistant to an antibiotic. The propagated vectors can then be removed from the *E. coli* cells and inserted into *Agrobacterium* cells containing a small Ti plasmid modified in a binary system, for transforming plant cells. Alternatively propagated vectors can also be used for other plant transformation techniques.

The term "vector" refers to a replicon, such as plasmid, cosmid, bacmid, phage or virus into which other gene sequences or elements (either DNA or RNA) can be connected to be replicated together with the vector. Preferably the virus derived vector is selected from bacteriophages, vaccinias, retrovirus or bovine papilloma virus. The "recombinant vector" results from a combination of chimeric genes commercial vector, or polynucleotide of the invention operably linked to an endogenous and/or heterologous polynucleotide of interest that is in turn operably linked to a termination signal. Such vectors may be obtained commercially, including Clontech Laboratories, Inc. (Palo Alto, Calif.), Stratagene (La Jolla, Calif.), Invitrogen (Carlsbad, Calif.), New England Biolabs (Beverly, Mass.) And Promega (Madison, Wis.). Examples of vectors used in the present invention, but without limitation, are the vectors pAC 321 and pMDC162 (Curtis and Grossniklaus, Gateway Cloning Vector for High-Throughput Functional Analysis of Genes in Plant., Plant Physiology, v. 33, n. 2, p. 462-469, 2003). The term "expression sequence enhancers" known as amplifiers ("enhancers") which may be very distant from the promoter (before or after, "upstream" or "downstream") and which enhance the transcription rate. These amplifiers are not specific and enhance the transcription of any promoter in its neighborhood. The efficiency of expression of a gene in a specific tissue depends on the proper combination and integration of amplifiers, promoters and adjacent sequences.

The first enhancer discovered that stimulated the transcription of eukaryotic genes was SV40 (present in the genome of Simian Virus 40). After the discovery of the SV40 enhancer, hundreds of other "enhancers" were identified, such as HSV-1, AMV, HPV-6, other viral genome into the DNA of eukaryotic cells. (Lodish et al, cell and molecular biology. $4^{th}$ edition page 368). The expression enhancers of the present invention can be, but are not limited to SV40, HSV-1, AMV, HPV-16.

The term "operably linked" means that the regulatory sequences necessary for expressing the coding sequence are placed in the DNA molecule in the appropriate positions relative to the coding sequence for the purpose of expressing the coding sequence. This same definition is sometimes applied to the arrangement of coding sequences and transcription controlling elements (e.g., promoters, helper or "enhancers" and termination sequences or elements) in the expression vector. An exogenous coding region is flanked by typically operably linked regulatory regions which regulate the expression of exogenous coding region in a transformed cell (which may be microorganism, plant or animal). A typical regulatory region operably linked to an exogenous coding region includes a promoter, i.e., a nucleic acid fragment which can cause transcription of exogenous encoding regions, located in the 5' region of the exogenous coding region. In the case of the present invention the regulatory region refers to regions substantially similar to SEQ ID NO: 1. To help increase transcription of a particular polynucleotide, the promoter sequence of the present invention may be linked to other regulatory sequences already described, such as: ATATT (strong expression in the root element), AACAAAC and GCCACCTCAT (details concerning the specific expression in seeds), GACGTG and CCTACC (both sequences can be stimulated to a stressor), among others. (Ai-Min Wu et al, Isolation of a cotton reversibly glycosylated polypeptide (GHRGPI) promoter and its expression activity in transgenic tobacco, Journal of Plant Physiology 163 (2006) 426-435). The regulatory sequences of the invention drive expression in any plant. More preferably the expression is directed to soybean plants.

A "termination sequence" is a DNA sequence that signals the end of the transcript. Examples of termination sequences, but are not limited to SV40 termination signal, polyadenylation signal of the HSV TK gene, nopaline synthase termination signal of *Agrobacterium tumefaciens* (NOS), termination signal of the octopine synthase gene, signal termination of the gene 19S and 35S CaMV, termination signal of corn alcohol dehydrogenase, gene termination signal of the mannopine synthase, gene termination signal of beta-phaseolin gene, termination signal of the ssRUBISCO gene, signal terminating the sucrose synthase gene, termination signal of the virus that attacks *Trifolium subterranean* (SCSV), the termination signal from *Aspergillus nidulans* trpC gene and the like. The present invention provides other regulatory regions of isolated polynucleotides that may be employed in handling plant phenotypes, together with isolated polynucleotides comprising such regulatory regions. More specifically the present invention relates to promoters or regulatory sequences that occur in soybean (*Glycine max*), responsible for the expression of the sulfotransferase putative flavonol protein throughout the plant, particularly in the root and seed. The isolated soy promoters were named in this invention PSulfT0.5 (SEQ ID NO: 1).

The amount of a polypeptide of particular interest may be increased or reduced by incorporating additional copies of genes or coding sequences encoding the polypeptide, operably linked to the promoter sequence of the present invention (SEQ ID NO: 1), into the genome of an organism such as a plant. Similarly, an increase or decrease in the amount of the polypeptide can be obtained by transforming the plant with antisense copies of such genes.

The polynucleotides of the present invention were isolated from soybean, specifically *Glycine max*, but it can alternatively be synthesized using conventional synthetic techniques. Specifically, the isolated polynucleotide of the present invention includes the sequence identified as SEQ ID NO: 1; the reverse complement of the sequence identified as SEQ ID NO: 1; and the reverse complement of the sequence identified as SEQ ID NO: 1.

Studies of the activity of the promoters of the present invention are detailed in the examples of this specification. Experimental data made in *Nicotiana tabacum* plants quantifying the GUS activity demonstrated that the recombinant vector containing the promoter PSulfT0.5 is able to drive the expression of the GUS gene constitutively, showing the promoter activity of the present invention.

The polynucleotide of the present invention can be synthesized using techniques which are well known in the art (Sambrook et al "Molecular Cloning, a laboratory manual", CSHL Press, Cold Spring Harbor, N.Y., 1989) The polynucleotide can be synthesized, e.g. using automated oligonucleotide synthesizers (e.g., OLIGO 1000M DNA synthesizer Beckman) to obtain polynucleotide segments of up to 50 or more nucleic acids. A plurality of such polynucleotide segments may then be ligated using standard DNA manipulation techniques that are well known in the art (Sambrook et al "Molecular Cloning, a laboratory manual", CSHL Press, Cold Spring Harbor, N.Y., 1989). A technique of conventional and exemplary polynucleotide synthesis involves the synthesis of a polynucleotide single-stranded segment having, for example, 80 nucleic acids, and hybridizing that segment to a segment 85 of complementary nucleic acids synthesized to produce an overhang of 5 nucleotides. The next segment may then be synthesized in a similar way as an overhang of 5 nucleotides on the opposite strand. The sticky or cohesive ends ensure a proper connection when the two portions are hybridized. Thus, the polynucleotides of this invention may be synthesized entirely in vitro.

As noted above, the promoter sequence of the present invention can be used in recombinant and/or expression vectors to drive the transcription and/or expression of a polynucleotide of interest in plants constitutively. The polynucleotide of interest may be endogenous or heterologous to an organism, e.g., a plant to be transformed. The recombinant and/or expression vectors of the present invention can thus be used to modulate transcription levels and/or expression of a polynucleotide, for example, a gene that is present in the wild-type plant, or may be used to provide a transcription and/or expression of a DNA sequence that is not found in the wild-type plant, including, for example, a gene encoding a reporter gene, such as GUS.

In some embodiments of the present invention, the polynucleotide of interest comprises an open reading frame encoding a polypeptide of interest. The open reading frame is inserted in the vector in a sense orientation and transformation with this genetic construct/recombinant vector will generally result in overexpression of the polypeptide selected in plants. The polypeptide of interest, which is regulated by the promoter of the present invention may be inserted into the vector in the sense orientation, antisense or in both directions. The transformation with a recombinant and/or expression vector containing the promoter of the invention regulating the expression of the polynucleotide of interest in antisense orientation or in both orientations (sense and antisense) will generally result in reduced expression of the selected polypeptide.

The polynucleotide of interest such as a coding sequence is operatively connected in a promoter sequence of the polynucleotide of the invention so that a host cell is capable of transcribing an RNA sequence driven by promoter linked to the polynucleotide of interest. The polynucleotide promoter sequence is generally positioned at the 5' end of the polynucleotide to be transcribed. Using specific promoters, such as the sequence of the promoter of the present invention identified as SEQ ID NO: 1, will affect the transcription of the polynucleotide of interest constitutively in plant transformed, hence the importance of the choice of the polynucleotide of interest.

The recombinant vector or expression vector of the present invention may also contain a selection marker that is effective in body cells, such as a plant, to allow detection of transformed cells containing the inventive recombinant vector. These markers, which are well known, typically confer resistance to one or more toxins. An example of this marker is the nptII gene whose expression results in resistance to kanamycin or neomycin, antibiotics which are usually toxic to plant cells in a moderate concentration. The transformed cells may thus be identified by their ability to grow in media containing the antibiotic in question. Other markers that can be used to construct recombinant vectors and/or expression containing the polynucleotide of the present invention can be, but are not limited to: hpt gene confers resistance to the antibiotic hygromycin, manA gene and the bar gene.

The system uses the manA gene (encoding the enzyme IMP—phosphomannose isomerase) of *Escherichia coli* (Miles and Guest, 1984. Complete nucleotide sequence of the smokes fumarase gene of *E. coli* Nucleic Acids Res 1984 Apr. 25; 12.(8): 3631-3642) with mannose as a selective agent is one of the systems suggested as alternative to the first two described above (Joersbo et al, 1998 interacting with mannose selection Parameters employed for the production of transgenic sugar beet, Physiologia. Plantarum Volume 105 Issue 1 Page 109—January 1999 doi: 10.1034/j.1399-3054.1999.105117.x). The plant species that do not metabolize mannose suffer from severe growth inhibition when it is offered as a sole carbon source in the culture medium. Adverse and inhibiting effects of the use of mannose are consequences of accumulation of mannose-6-phosphate product from the phosphorylation of mannose by a hexokinase. PMI promotes interconversion of mannose-6-phosphate and fructose 6-phosphate, thus enabling the first to be catabolized in the glycolytic pathway (Ferguson and Street, 1958). Analysis system marker gene/selective agent for alternative positive selection of somatic embryos GM papaya, Rev. Bras. Fisiol. Veg., 2001, vol. 13, no. 3, p. 365-372. ISSN 0103-3131: Malca et al., 1967 Advances in the selection of transgenic plants using non-antibiotic marker genes, Physiologia *Plantarum* Volume 111 Issue 3 Page 269—March 2001 doi:10.1034/j.1399-3054.2001.1110301.x). The bar gene (encoding the enzyme PAT—phosphinothricin-N-acetyltransferase) de *Streptomyces hygroscopicus* (Murakani et al., 1986 The bialaphos biosynthetic genes of *Streptomyces hygroscopicus*: molecular cloning and characterization of the gene cluster. Molecular and General Genetics., 205: 42-50, 1986.), and glufosinate ammonium (PPT) as selective agent, it is among the systems type herbicide tolerance gene, one of the most widely employed by genetic engineering in developing plant GMOs. PAT deactivates herbicides presenting the PPT as active compound by detoxification of latter. The detoxification, resulting from the acetylation of the free amino grouping present in PPT, renders it unable to compete in an inhibitory manner with the glutamine synthetase (GS), thereby enabling the removal of toxic ammonia from the plant cell by converting glutamate to glutamine, and this reaction is catalyzed by GS (Lindsey, 1992 Molecular cloning of ICAM-3, a third ligand for LFA-1, constitutively expressed on resting leukocytes, Nature 360, 481-484 (Dec. 3, 1992); doi:10.1038/360481a0).

Alternatively, the presence of the chimeric gene in transformed cells may be determined by other techniques known in the art (Sambrook et al "Molecular Cloning, a laboratory manual", CSHL Press, Cold Spring Harbor, N.Y., 1989), such as Southern and PCR.

Techniques for operatively linking the components of inventive recombinant or expression vectors are well known in the art and include the use of synthetic linkers containing one or more restriction endonuclease sites as described, for example, in Sambrook et al ("Molecular Cloning, a laboratory manual", CSHL Press, Cold Spring Harbor, N.Y., 1989). Chimeric genes of the present invention can be linked to a vector having at least one replication system, e.g., *E. coli*, thus after each manipulation, the resulting constructions can be cloned and sequenced.

The expression cassettes of the present invention can be used to transform a variety of organisms including, but not limited to plants. Accordingly, cells, plant tissues or genetically-modified plants expressing genes of interest regulated by promoters previously described are also embodiments of the invention. Plants that may be transformed using the recombinant and/or expression vectors of the present invention include monocotyledonous angiosperms (e.g., grasses, corn, grains, oats, wheat and barley . . . ), dicotyledonous angiosperms (e.g., soybean, arabidopsis, tobacco, vegetables, alfalfa, oats, eucalyptus, maple . . . ), and gymnosperms (such as pine, spruce white, larch . . . ). Plant transformation protocols are already well known in the art (Manual of genetic transformation of plants. Brasilia: EMBRAPA-SPI/EMBRAPA-CENARGEM, Chapters 3 and 7, 1998). In a preferred embodiment, the recombinant and/or expression vectors of the present invention are used to transform dicotyledonous plants. Preferably, the selected plant is of the Fabaceae family, more preferably the species *Glycine max*. Other plants may be usefully transformed with the recombinant and/or expression vectors of the present invention include, but are not limited to: *Anacardium, Annona, Arachis, Artocarpus, Asparagus, Atropa, Avena, Brassica, Carica, Citrus, Citrullus, Capsicum, Carthamus*, Coconuts, *Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea*.

The transcription termination signal and polyadenylation region of the present invention include, but are not limited to, the SV40 termination signal, the polyadenylation signal of the HSV TK termination signal of the nopaline synthetase gene of *A. tumefaciens* (nos), the termination signal of CaMV 35S RNA gene of the virus that attacks the termination signal *Trifolium* subterranean (SCSV), the termination signal *Aspergillus nidulans* trpC gene and the like. Preferably, the terminator used in the present invention is the terminator from the gene encoding the protein nopaline synthase of *Agrobacterium tumefaciens*.

The expression cassettes of the invention can be introduced into the genome of the desired plant host by a variety of conventional techniques. For example, introduction mediated *A. tumefaciens*; electroporation; protoplast fusion; injection into reproductive organs; injection into immature embryos; microinjection of plant cell protoplasts; using ballistic methods, such as bombardment with DNA-coated particles and the like. The choice of technique will depend on the plant being transformed. For example, dicotyledonous plants and certain monocots and gymnosperms may be transformed by *Agrobacterium* Ti plasmid technology. Recombinant and/or expression vectors may be combined with appropriate flanking T-DNA regions introduced into conventional host vector *Agrobacterium tumefaciens*. The virulence function of the host *Agrobacterium tumefaciens* will direct the insertion of the gene constructions and adjacent marker into the plant cell DNA when the cell is infected by the bacteria. Technical transformation mediated by *Agrobacterium tumefaciens*, including disarming and use of binary vectors, are well described in the scientific and patent literature (as mentioned in US patent application 20020152501, Horsch et al, Science 233: 496-498, 1984; and Fraley et al, Proc Natl Acad Sci USA. 80:4803, 1983).

Microinjection techniques are known in the art and well described in scientific and patent literature. The introduction of recombinant and/or expression vectors using polyethylene glycol precipitation is described in Paszkowski et al. Embo J. 3:2717-2722, 1984 (as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501). The introduction of recombinant and/or expression vectors of the present invention can be made in tissues such as leaf tissue, dissociated cells, protoplasts, seeds, embryos, meristematic regions, cotyledons, hypocotyledons, and others. Preferably the present invention utilizes the transformation by introducing mediated *A. tumefaciens* using *Nicotiana tabacum* with a model plant (modified by BARROS, L. M. G. Genetic transformation of *Nicotiana tabacum* cv Xanthi using *Agrobacterium tumefaciens* and electroporation. Master's thesis. University of Brasilia, DF, Brazil, 117p, 1989). However, other processing methods may be used to insert recombinant and/or expression vectors of the present invention, such as the biolistic consisting of a direct transformation technique of DNA that utilizes microprojectiles propelled at high speed for carrying DNA into cells [Rech, E. L; Aragao, F. J. L. Biobalistica. In: Manual of Genetic Transformation in Plants (Brasileiro, A. C. M. & Carneiro, V. T. C. eds.), EMBRAPA Information Production Service—SPI. 1998, 106pp], and via pollen tube. The method of pollen tube pathway transformation was first disclosed by Zhou et al (Zhou, G., Wang, J., Zeng, Y., Huang, J., Qian, S., and Liu, G. Introduction of exogenous DNA into cotton embryos Meth Enzymol 101:433-448, 1983), and involves the application of a DNA solution on top of the young apple after pollination. Using this technique, the exogenous DNA can reach the ovary through the passage left by the pollen tube and integrate the zygotic cells already fertilized but not divided.

Once the cells are transformed by any of the techniques mentioned above, cells with the recombinant and/or expression vector of the present invention incorporated into their genome can be selected by means of a marker such as the hygromycin or kanamycin resistance marker. The transformed plant cells may then be cultured to regenerate a whole plant which possesses the transformed genotype and finally the desired phenotype. Such regeneration techniques rely on manipulation of certain phytohormones in tissue culture growth, typically containing a biocide and/or herbicide marker which must be introduced together with the desired nucleotide sequence. Plant regeneration from protoplast cultures is described in Evans et al. (Evans et al, protoplasts Isolation and Culture, Handbook of Plant Cell Culture, pp 124-176, MacMillilan Publishing Company, New York, 1983; and Binding, Regeneration of Plants, Plant Protoplasts pp 21-73, CRC Press. Boca Raton, 1985 as mentioned in the application of patent US20020152501).

Regeneration can also be obtained from plant callus, explants, organs, or part thereof. Such regeneration techniques are well described in the art, such as in Leelavathi et al. [Leelavathi et al, A simple and rapid *Agrobacterium*-mediated transformation protocol for cotton (*G. hirsutum* L): Embryogenic calli as a source to generate large numbers of transgenic plants, Plant Cell Rep (2004) 22:465-470]. This paper describes a protocol for transformation and regeneration of the cotton embryogenic callus where *Agrobacterium* is grown under stress, dehydration and antibiotic selection for 3 to 6 months for the regeneration of various transgenic embryos, an average of 75 globular embryos. As observed on the selection plates these embryos are grown and multiplied on the medium, followed by the development of cotyledonary embryos in an embryo maturation medium. To obtain an average of 12 plants per Petri dish of co-cultured calli. Approximately 83% of these plants are transgenic. The resulting transformed plants may be reproduced sexually or asexually or using methods known in the art [Leelavathi et al, A simple and rapid *Agrobacterium*-mediated transformation protocol for cotton (*Gossipium hirsutum* L): Embryogenic calli as a source to generate large Numbers of transgenic plants, Plant Cell Rep, 2004, 22: 465-470], to give successive generations of transgenic plants.

The production of RNA in cells may be controlled by choice of the promoter sequence by selecting the number of functional copies or by incorporating the polynucleotides integration site in the host genome. An organism can be transformed using a recombinant and/or expression vector of the present invention containing more than one open reading frame encoding a polypeptide of interest.

The isolated polynucleotide of the present invention also has utility in genome mapping, in physical mapping, and in positional cloning of genes. The sequence identified as SEQ ID NO: 1 and variants thereof can be used to design oligonucleotide probes and primers. The oligonucleotide probes designed using the polynucleotides of the present invention can be used to detect the presence of promoters in any organism having sufficiently similar DNA sequences in their cells using techniques well known in the art such as dot blot DNA hybridization techniques (Sambrook, J., Fritsch, E F, Maniatis, T., Molecular Cloning a laboratory manual $2^{nd}$ edition [M] New York: Cold Spring Harbor Laboratory Press, 1989).

The regulatory regions are utilized as an important tool to target the expression of genes of interest, such as those encoding toxic Cry-type proteins for generating new lines of genetically-modified (GM) plants resistant to insect attack.

The polynucleotide of the present invention is able to change the efficient expression of one or more genes of interest in plants, particularly the Glycine genus. The possibilities of using the invention are broad, highlighting promoter use in processes for generating transgenics requiring constitutive expression at high levels such as: 1) transgenes, which confer herbicide resistance, 2) more nutritious fodder plants, 3) transforming plants with multiple transgenes, 4) in case of incompatibility of expression system for a plant with regulatory sequences of viral origin.

The advantage of having a promoter sequence obtained from the genome of a plant, and that it can be used in other plant species, reduces environmental and health risks, and improves acceptance by the consumer market. The speed in getting the promoter sequence and making it available for use, as well as its effectiveness in regulating gene expression, favors the use of this promoter compared to other obtained from viruses, bacteria, among others.

The illustrative examples presented below will serve to better describe the present invention. However, illustrated data and procedures relate merely to certain embodiments of the present invention and should not be taken as limiting the scope thereof. When gene expression promoters have proven regulating gene sequences in transformed plants, this construct (promoter and/or resistance gene, for example) obtained from the genome of the same species that will be inserted, increases the likelihood of successful transformation event. Moreover, obtaining genes and promoters from the soy itself indicates a lower risk path for the environment and health when working with promoters or genes from viruses, bacteria for example. The strategy of obtaining the promoter of the present invention can be verified by FIG. 1 and will be further detailed in the examples.

EXAMPLES

Example 1—Identification of Organ-Specific Contigs

Virtual contrasts (electronic Northern) to identify specific and abundant root sequences were made in ESTs database (expressed sequence tags) of soy (alanine.cenargen.embrap-a.br/Soja001) of Embrapa Genetic Resources and Biotechnology. The bank contains contigs formed from ESTs available in the public domain (Shoemaker et al, A Compilation of soybean ESTs: Genome generation and analysis, v 45, n 2, p 329-338, 2002) and has a tool for conducting virtual Northern using the Fisher's exact test to determine the statistical significance ($P \leq 0.05$) of the results. By this tool it is possible to obtain the frequency ESTs forming a contig (a putative transcript sequence). The libraries of cDNA sequences from root were grouped and contrasted with the sequences of cDNA libraries of other bodies. Thus, contrasts were performed between the root versus (vs.) non-root groups. Undifferentiated tissue and seedling cDNA libraries were not entered in any group.

Example 2—Virtual Analyses of Contigs Organ-Specific

The nineteen (19) resulting electronic Northern contigs, considered here as putative candidate genes, were compared using BLASTn (Altschul et al, Gapped BLAST and PSI- BLAST: A new generation of protein database search programs Nucleic Acids Research, Vol. 25, n 17, p 3389-402, 1997) with the sequences present in the genome structural database of soybeans, consisting of sequences obtained during the execution of the Soybean Genome Project (GenoSoja) (bioinfo03.ibi.unicamp.br/soja/). This database uses the Audic-Claverie significance test (Audic and Claverie, The Significance of Digital Gene Expression Profiles. Genome Res, v. 7, n. 10, p. 986 to 95.1997.) to determine the frequency of ESTs within the different libraries. Accordingly, the contigs obtained by the electronic Northern carried out at the Embrapa Genetic Resources and Biotechnology database that had corresponding sequences in GenoSoja bank were again analyzed for their expression profile.

Figure 2:
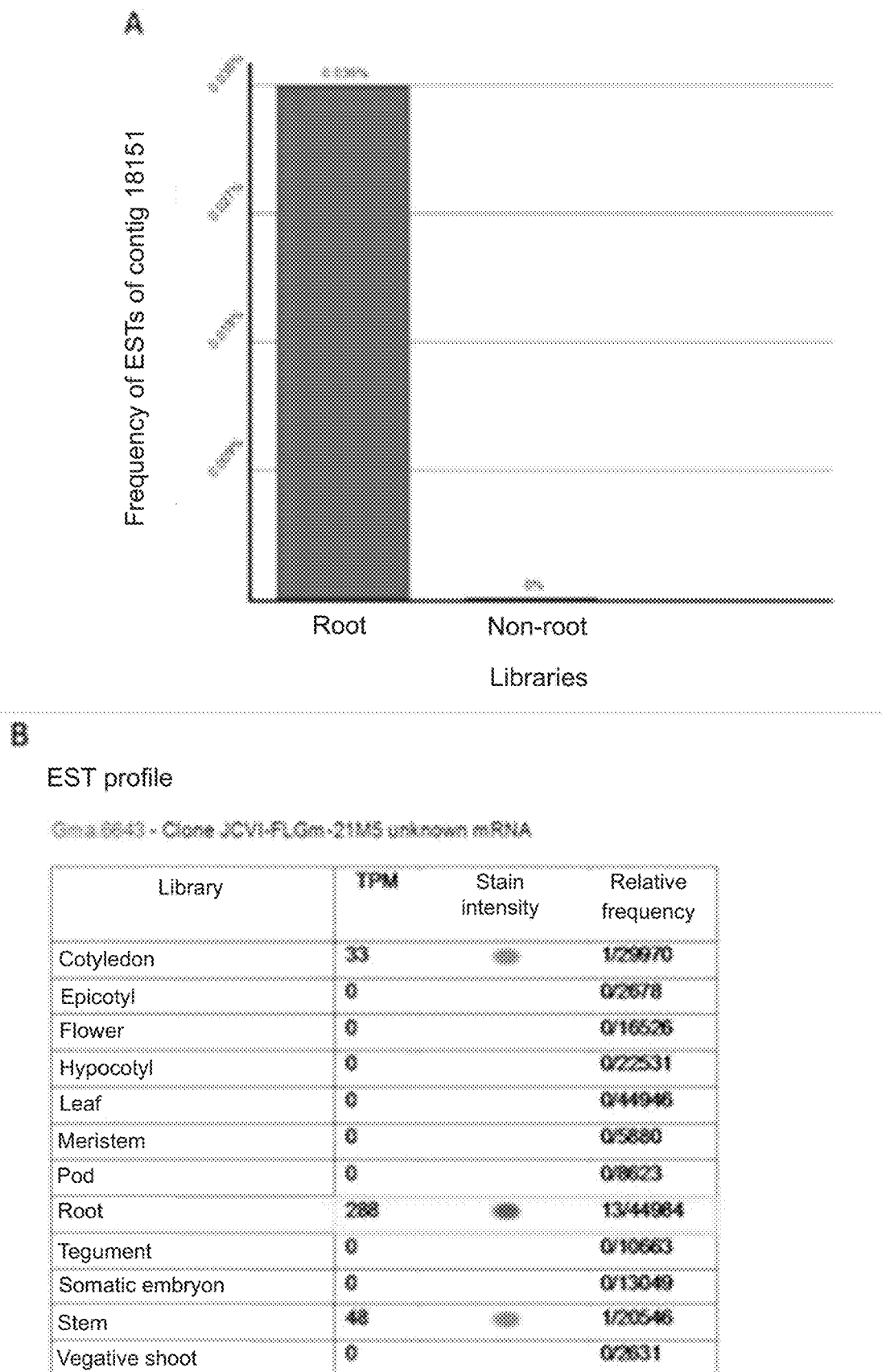
FIG. 2. Contig 8703 expression profile based on the relative frequency of ESTs (expressed sequence tags) (ESTs of the contig/total library of ESTs). (A) frequency of ESTs that make up the contig 8703 from root and non-root (leaf flower, seed and pod) soybean libraries of the Embrapa Genetic Resources and Biotechnology bank (alanine.cenargen.embrapa.br/Soja001/); (B) expression profile of Gma 6643 gene (identical to 8703) originating from the respective libraries of the NCBI UniGene sequence database (www.ncbi.nlm.nih.gov/UniGene/ESTProfileViewercgi?uglist=Gma.6643), indicating the name of the libraries, the number of transcripts per million (NTM); the estimated intensity of the stain based on NTM and the relative frequency.

The selected contigs were compared to the bank's non-redundant sequences from NCBI (www.ncbi.nlm.nih.gov) using the BLASTn (Altschul et al, Gapped BLAST and PSI-BLAST: a new generation of protein database search programs. Nucleic Acids Research, v. 25, n. 17, p. 3389-402, 1997). Thus, the transcripts were found (CDS) to match (100% sequence identity) the contigs in this bank. Transcripts identical to contigs were also analyzed at Unigene www.ncbi.nlm.nih.gov/UniGene/) on the expression profile. According to the electronic Northern carried out at the Bank of Embrapa Genetic Resources and Biotechnology, the most promising was the contig 8703, in that it consists only of sequences derived from root libraries (FIG. 2a). The Gma 6643 gene corresponding to this contig in NCBI also presented in UniGene the expression profile based on preferred EST Root and reduced expression in cotyledon and stem (FIG. 2b).

The undifferentiated tissue cDNA libraries were disregarded in these analyses.

Example 3—Functional Annotation and Mapping

Figure 3:
FIG. 3. Comparative analysis of the sequence of the contig 8703, 1043 pb, with the soybean genome in the Phytozome (www.phytozome.net/). The Glyma13g26070.1 transcript of the chromosome Gm13 that aligned with contig 8703 (in black) being 100% identical is indicated in white.
Figure 4:
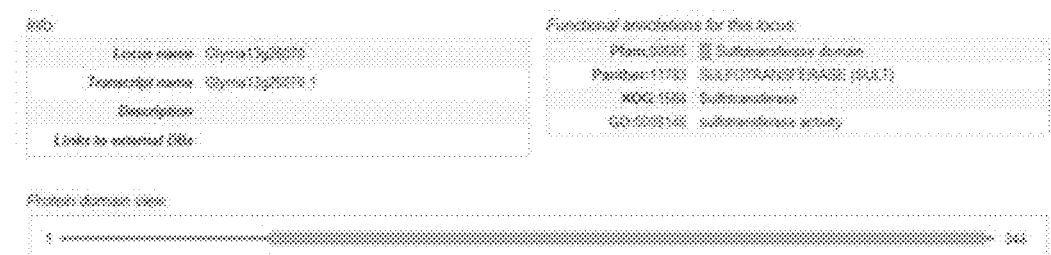
FIG. 4. Functional annotation of the locus that Glyma13g26070.1 corresponding to contig 8703 in the Phytozome database (www.phytozome.net/).

The contigs that showed preferential expression in root in at least two of the three banks used (alanine.cenargen.embrapa.br/Soja001; bioinfo03.ibi.unicamp.br/soja and www.ncbi.nlm.nih.gov/UniGene/) were aligned using the BLASTn (Altschul et al., Gapped BLAST and PSI-BLAST: a new generation of protein database search programs. Nucleic Acids Research, v. 25, n. 17, p. 3389-402, 1997) into the genome of soybean cv. Williams 82 (Schmutz et al., Genome sequence of the palaeopolyploid soybean. Nature, v. 463, n. 7278, p. 178-183, 2010.) available at the Phytozome genome bank (www.phytozome.net/). The bank provides information about the mapping of the genome transcribed through GBrowse and functional annotation of these data with the annotation platforms: Pfam, Panther, KOG, GO. Although no similar sequence to contig 8703 was found on the structural soybean genome database, the sequence of the corresponding gene (100% identity) to the contig was located in the soybean genome (Phytozome: www.phytozome.net/) and its functional annotation obtained (FIGS. 3 and 4).

Example 4—Experimental Validation: RT-PCR

For experimental validation the putative candidate gene named GmSulfTI (*Glycine max* Sulfotransferase1—in reference to the functional annotation of Glyma13g26070 locus) was selected due to its high degree of specificity and high level of expression in root. This gene corresponds to the contig 8703. The experimental validation of GmSulfTI gene was performed by means of temporal and spatial expression assays using the techniques of: a) RT-PCR (Reverse transcriptase-PCR); b) Northern Blot.

To perform the RT-PCR assays (Reverse Transcriptase-Polymerase Chain Reaction) total RNA samples were extracted from roots, young leaf, mature leaf, pod stages in R4, R5 and R6 R5 and seed in stages, R6 and R7 individually extracted from plants *Glycine max* cv. Conquista. The RNA was extracted using a method described by Jones et al (Jones et al., High levels of expression of introduced chimeric genes in regenerated transformed plants EMBO Journal. 4: 2411-2414, 1985. The pods were collected from plants in the reproductive stages R4, R5 and R6 and seeds in stages R5, R6 and R7 (Fehr and Caviness, Stages of Soybean Development Ames: Iowa State University of Science and Technology, vol 80, p 1-12, 1977). These stages were determined based on flowering, development of pods and seed and plant maturation, according to Fehr and Caviness (Stages of Soybean Development. Ames: Iowa State University of Science and Technology, v. 80, p. 1-12, 1977). In stage R4, the pod has cm 2. In others, the pods are identified in accordance with the development of the seed. In stage R5, the seed has 3 mm in R6 the green seed cavity fills the cavity of the pod, and R7 is the beginning of maturity, in which the pod has a brownish color and the seed has reached its final size, but not its color. Two grams of each organ were weighed, immediately frozen in liquid nitrogen and stored at −80° C. The seeds and pods were separated before freezing.

Then the RNAs were examined for integrity, in denaturing gel, 1.5%. The RNA samples of root, leaf, pod and seed were used as template in the formation of cDNA molecules by RT-PCR reactions using oligo dT primers. The CDNAs obtained were used in PCR reactions with specific primers specific for the gene GmSulfTI in order to evaluate its expression. To this end, the following specific oligonucleotides were designed with the help of the Primer3 program (frodo.wi.mit.edu/primer3/) (Rozen & Skaletsky, Primer3 on the WWW for general users and for biologist programmers. Methods in Molecular Biology, v. 132, p. 365-86, 2000).

TABLE 1

Sequences of the specific primers used in the semiquantitative RT-PCR reactions.

| Gene | Initiator | Sequence | Fragment size to be amplified |
|------|-----------|----------|-------------------------------|
| GmSulfT1 | RzGmSdF3 | SEQ ID NO: 2 | 423 pb |
|  | RzGmSdR4 | SEQ ID NO: 2 |  |

The total RNA extracted was treated with DNase I Amplification Grade (Invitrogen™). Samples of 5 μg RNA were treated reaction containing 10× Reaction Buffer DnaseI, 5 units of DNase I Amplification Grade (1 U/μL) and DEPC-treated water in a final volume of 10 μL. The reaction was incubated at 25° C. for 15 minutes. The enzyme was inactivated by adding EDTA to a concentration of 12.5 mM followed by heating at 65° C. for ten minutes.

The first cDNA strand was synthesized by reverse transcription of RNA from root, leaf, pod and soybean plant seed using the SuperScript III Reverse Transcriptase enzyme (Invitrogen™) according to manufacturer's protocol. In microfuge tubes 300 ng of oligo (dT), 2 μg RNA of an organ treated with DNase and 0.8 mM of each dNTP (deoxyribonucleotide triphosphate) were initially added. The reaction was kept at 65° C. for five minutes. Then the First-strand 1× buffer, 5 mM DTT and 200 units reverse transcriptase was added. The synthesis occurred at 50° C. for one hour. This procedure was performed for the cDNA synthesis from total RNA extracted from each organ. The products of the reactions were diluted 20-fold and 5 µL was used in the PCR reactions.

Figure 5:
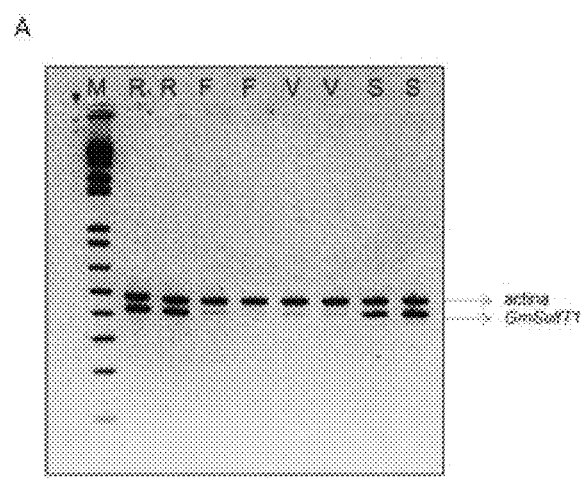
FIG. 5. Expression profile of the GmSulfT1 gene. Electrophoresis in agarose gel 1.5% of the products of the semiquantitative RT-PCR reactions done in reaction duplicates, indicating the amplified fragments of actin gene (~500 pb) and GmSulfT1 (423 pb) in the root (R); leaf (F); pod (V) or seed (S). M: 1 Kb plus DNA LADDER.

For a semiquantitative RT-PCR reaction, apart from the specific primer pair (Table 1) for the target transcript, another primer pair was used to amplify a fragment of the actin gene, a constitutively expressed gene. All PCRs were set up in duplicate reaction for each cDNA of root, leaf, pod or seed containing the following reagents: 1×PCR buffer, 0.4 mM of each dNTP (Invitrogen™), 0.4 µM each primer mentioned above, 1.5 units Taq polymerase (Invitrogen™), 5 µL of diluted cDNA, 3 mM MgCl 2 and sterile water (Milli-Q) in a final volume of 25 µL. The PCR conditions were: 94° C. for one minute followed by cycles of 94° C. for 30 seconds, 55-57° C. for 30 seconds and 68° C. for two minutes. The PCR (15 µL) products were separated into 2% agarose gel stained with ethidium bromide and visualized under ultraviolet (UV) light. The number of PCR cycles was optimized to ensure that the amplification reactions were stopped in the exponential amplification phase of the product. The identity of the amplified product was confirmed by the electrophoretic migration of the fragments compared to the molecular weight marker (FIG. 5).

Example 5—Experimental Validation: Northern Blot

Samples of the total RNA root, young leaf, mature leaf and pod, extracted as described in Example 4 were fractionated in agarose gel 1.5% under denaturing conditions (formaldehyde) and MOPS buffer (MOPS 0.2M, AcNa 50 mM, EDTA 10 mM). In each well of the gel, there was placed 20 µg of total RNA dissolved in sample buffer (30% ficol, EDTA 0.5M pH 8.0, bromophenol blue 0.025%, formamide 30.1%, glycerol 2% and ethidium bromide 0.1%). After electrophoresis, the total soybean RNA was vacuum transferred to nylon membrane (Hybond—N, Amersham Bioscience). The transfer buffer used was 10×SSPE (NaCl, 1.5M; NaH2PO4 0.1M; Na2-EDTA-2H2O 10 mM). The transfer was performed for four hours at a pressure of 5 mm Hg. Finally, the membrane was incubated for five minutes in 2×SSPE and RNA was fixed to the membrane by exposure to UV light (UV Stratalinker 1800—Stratagene) for 30 seconds.

The Northern blot probes were performed with the same fragments obtained from the RT-PCR, whose products had approximately 400 bp (Table I). Fragments were purified using the Wizard SV Gel Kit® and Clean-Up System (Promega). Fifty ng of each fragment were denatured for five minutes at 95-100° C. and incubated on ice for a further five minutes. Then, the denatured fragment was added to the marking kit Ready to Go kit (Amersham Bioscience) together with 5 µL of dCTP α-P32 (50 µCi), as per the manufacturer's specifications. The reaction was incubated at 37° C. for 40 minutes. After the period the probe was denatured for five minutes at 95-100° C. and immediately placed on ice for ten minutes. Then the probe was added to the membrane containing the RNA previously pre-hybridized with the hybridization buffer ULTRAHyb Ultrasensitive (Applied Biosystems) at 42° C. for four hours. Hybridization occurred overnight at the same temperature.

Figure 6:
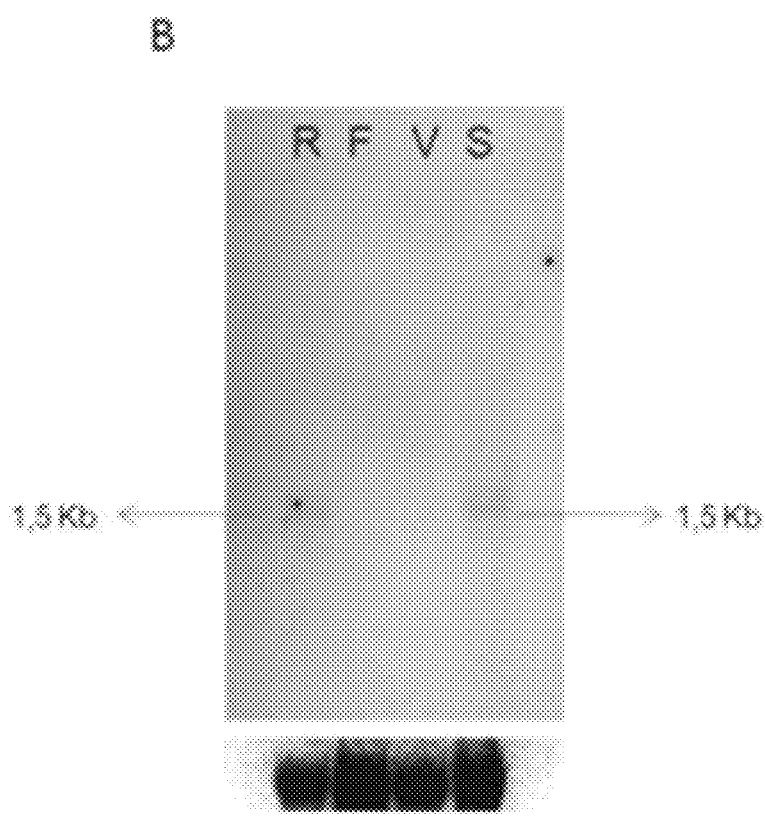
FIG. 6. Northern blot assay of GmSulfT1 with total RNA from soybean organs, presenting 1.5 Kb fragment corresponding to the estimated size of the GmSulfT1 transcript. In the lower panel, electrophoresis in agarose gel 1.5% showing 25S ribosomal RNA concentration equivalents in the corresponding samples, after staining with ethidium bromide. Root (R); leaf (F); pod (V) or seed (S).

The membrane was washed at 42° C. twice for 15 minutes with 2× washing solution (SSC 2×, SDS 0.1%) and twice with 0.1× washing solution (SSC 0.1×, SDS 0.1%). Then it was exposed to Imaging Plate (IP BAS-SR 2040) for about four hours, at which time the radioactivity present in the membrane was captured and photodocumented by the equipment FLA 3000 (Fujifilm). The result can be seen in FIG. 6.

According to the validation analyses by RT-PCR and Northern blot, the gene GmSulfTI is preferentially expressed in seed and root. From these analyses, it is now regarded as a candidate gene for isolation of its promoter, as its promoter region may have domains that direct the gene expression to root.

Example 6—Promoter Isolation

Figure 7:
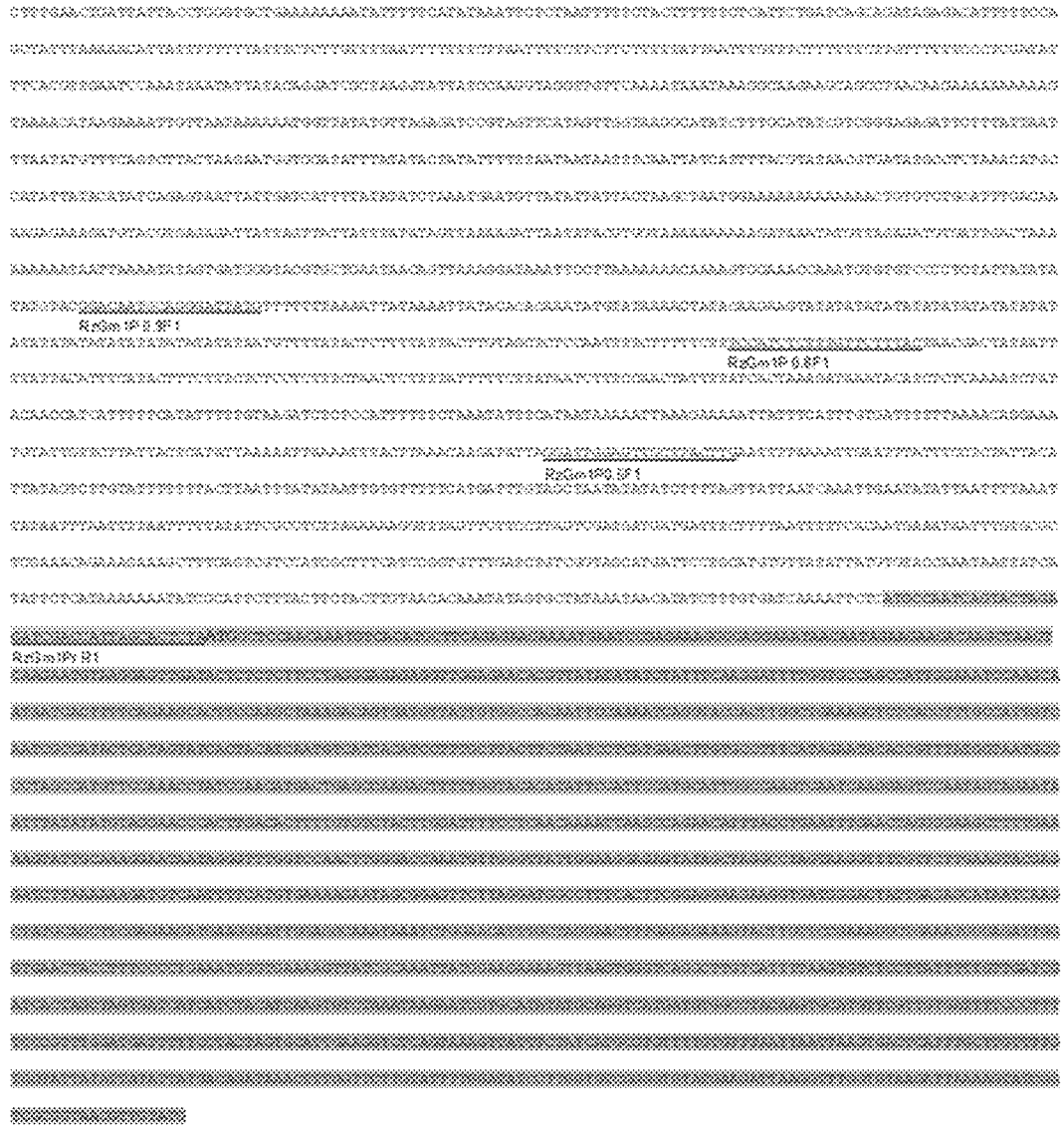
FIG. 7. Genomic sequence of the promoter and coding region of GmSulfT1 of *G. max*. cv. Williams 82 obtained by the Phytozome (www.phytozome.net/) (SEQ ID NO: 8). The translation initiation site (ATG) is highlighted in bold and the gray regions correspond to region 5' UTR, to the coding sequence and to the region 3'UTR, in this order. The regions where the primers enchain for amplification of the various promoter fragments are underlined.

Through the phytozome database (www.phytozome.net) it was possible to obtain the sequence of the upstream region of the coding sequence (CDS) of gene GmSulfTI for the isolation of its promoter region. Thus, the promoter was identified by mapping the genes selected in GBrowse (www.phytozome.net/cgi-bin/GBrowse/soybean) from the soybean genome cv. Williams 82 (Schmutz et al., Genome sequence of the palaeopolyploid soybean. Nature, v. 463, n. 7278, p. 178-183, 2010). Thus, the 3000 bp upstream of the 5' end of GmSulfTI CDS (Glyma13g26070.1) were used for the primer design. Fragments were amplified with primers specifically designed to generate fragments of different sizes, but always containing the 5' UTR region of the transcript and the start of the promoter region (Table 2). The size of the fragments depended on the design of favorable sequences of the primers. FIG. 7 shows the regions where the initiators enchain (underlined) to amplify promoter fragments of the gene GmSulfTI. Thus, to amplify the fragments, the same antisense primer and different sense primers were used.

TABLE 2

Sequence of primers used in the cloning of the promoters and deletions 5' of the gene GmSulfT 1.

| Promoter region of the gene | Initiator | Sequence | Size of the product |
|---|---|---|---|
| GmSulfT1 | RzGm1P0.9F1 | SEQ ID NO: 4 | 985 pb - PSulfT0.9 |
| | RzGm1P0.8F1 | SEQ ID NO: 5 | 810 pb - PSulfT0.8 |
| | RzGm1P0.5F1 | SEQ ID NO: 6 | 505 pb - PSulfT0.5 |
| | RzGm1PrR1 | SEQ ID NO: 7 | R |

R: antisense primers.

Example 7—Cloning the Promoters

Figure 8:
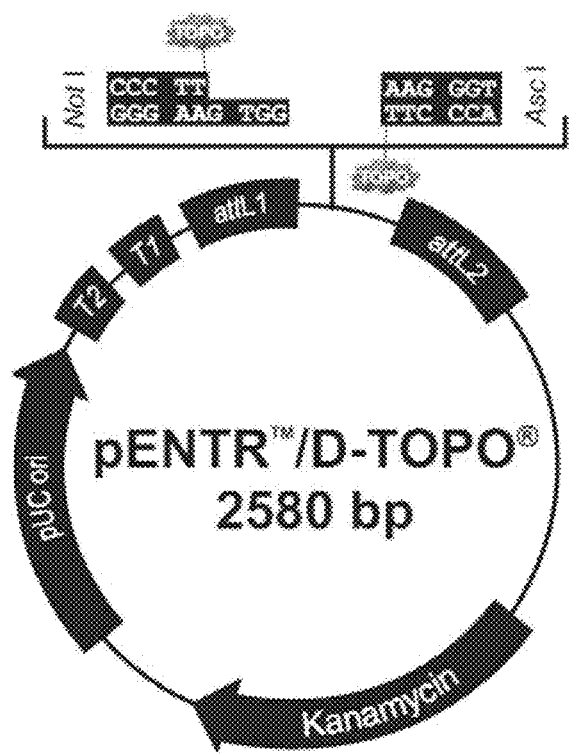
FIG. 8. Schematic representation of the vector pENTR™. The site in which the DNA fragment is linked, such that it is flanked by the recombination sites attL1 and attL2, is highlighted in the diagram. Source: Invitrogen™ (Invitrogen™, pENTR™ Directional TOPO® Cloning, 2006) FIG. 9. Schematic representation of the vector pMDC162. The drawing shows the coding regions that make up the vector, its restriction map and the recombination sites attR1 and attR2. Recombination between sites attL1 and attL2 of the input vector with sites attR1 and attR2 (indicated by arrows) of the target vector will result in the insertion of the DNA fragment of interest and in the excision of the killer gene ccdB. Source: Curtis and Grossniklaus (A Gateway Cloning Vector Set for High-Throughput Functional Analysis of Genes in Plant. Plant Physiology, v. 133, n. 2, p. 462-469, 2003).
Figure 9:
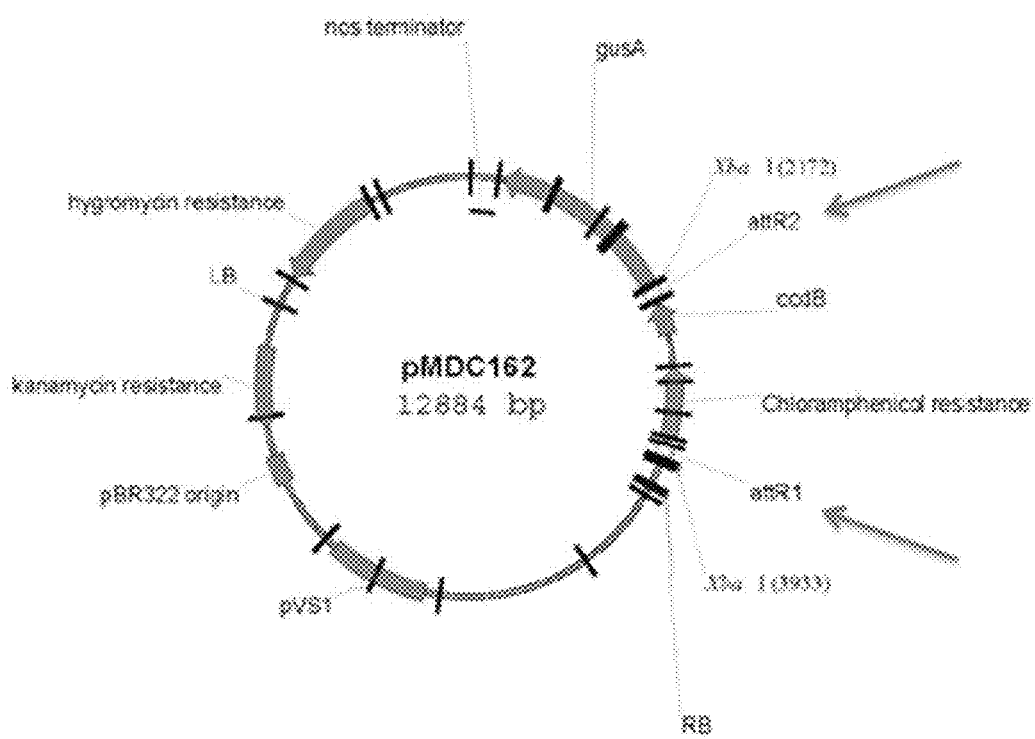

The fragments of the promoter region were cloned in binary vector by through the Gateway® system based on site-specific recombination of bacteriophage λ. This system consists of transferring a DNA fragment inserted into an input vector for a vector destination by means of site-specific recombination. Accordingly, the attl_1 and attl_2 sites flanking the region of the DNA to be transferred into the input vector recombine, respectively, with attr1 and attR2 sites present in the target vector and that flank the lethal ccdB gene. After the reaction, the input vector will contain the lethal gene and the target vector contains the DNA fragment of interest. The plasmid pENTR™ (FIG. 8) was used as input vector and as destination vector the binary plasmid PMDC 62 (FIG. 9) specific for use in *Agrobacterium*. The primers designed from the genomic sequence (Table 2) were used to amplify the various fragments of the promoter region. The enzyme Platinum Pfx DNA Polymerase (Invitrogen™) was used to catalyze the reaction, according to the following protocol: enzyme buffer 1× buffer, 0.3 mM of each dNTP, 2 mM MgSO4, 0.2 μM of each primer, 500 ng genomic DNA and 0.5 U of Pfx in the final volume of 25 μL. The same antisense primer was combined with all sense primers of the respective promoter to generate different fragments from the 5' region (Table 2). The PCR had the following parameters: 94° C. for three minutes, followed by 38 cycles of 94° C. for 30 seconds, 53° C. for 30 seconds and 68° C. for two minutes.

The amplicons were ligated to the vector pENTR™/D-TOPO® (Invitrogen™) in a reaction with a final volume of 6 μL containing from 0.5 to 4 μL of the PCR product, 1 μl of saline and 1 μL of the TOPO® vector. The reaction was incubated for ten minutes at ambient temperature and subsequently used in the heat shock transformation of competent cells of *Escherichia coli* One Shot® TOP10 (Invitrogen™) in conformity with the manufacturer's specifications. Initially, 2 μl of the ligation reaction was added to the microfuge tube containing the cells in stock. The system was incubated on ice for five minutes and then at 42° C. for 30 seconds. Immediately after heat shock, 250 μL of SOC medium (Sambrook and Russell, Molecular Cloning—A laboratory manual 3. New York: Cold Spring Harbor Laboratory Press, 2001) was added to the microfuge tube and the culture was incubated at 37° C. for one hour. The cells were spread on Petri dishes with LB agar medium-solid (Sambrook and Russell, Molecular Cloning—A laboratory manual 3. New York: Cold Spring Harbor Laboratory Press, 2001) and kanamycin [50 μg/mL] and incubated at 37° C. for 14 hours.

The primary building fragment of the promoter region linked to the pENTR™ vector is the input vector and the cells transformed with it are the input clones.

Example 8—Extraction of Plasmidial DNA

Figure 10:
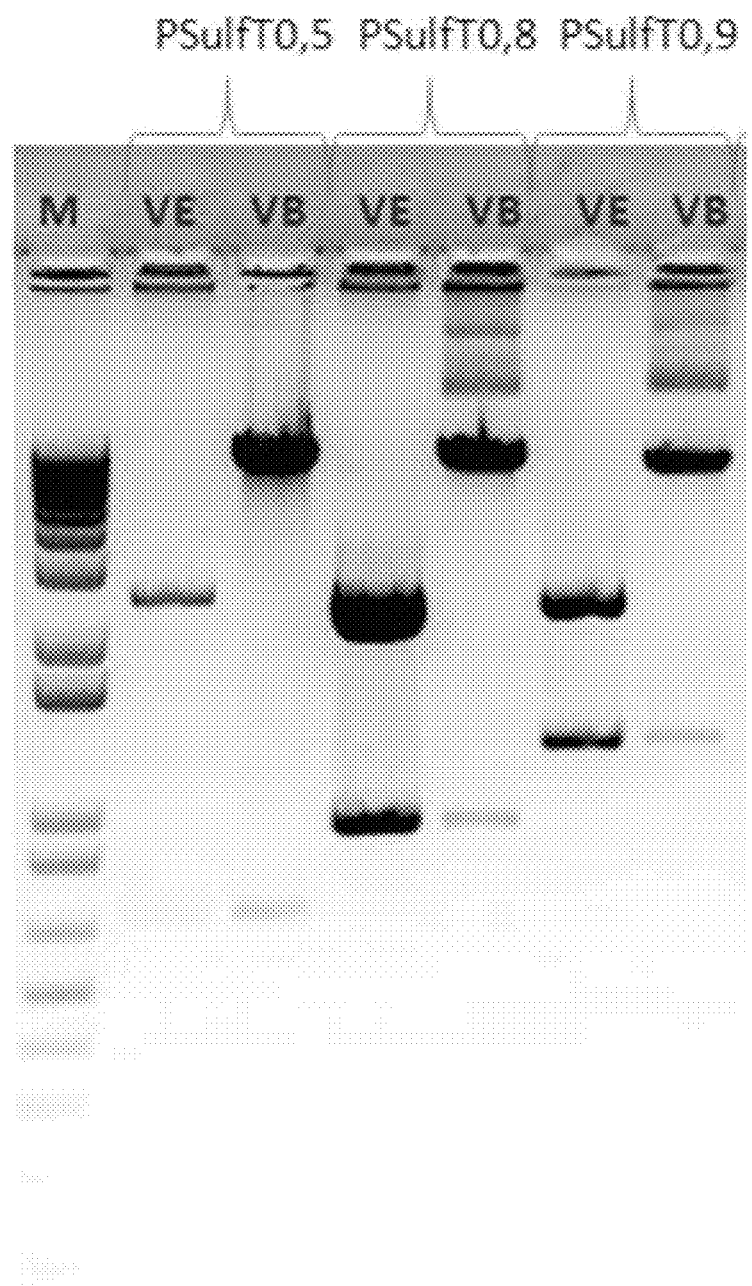
FIG. 10. Electrophoretic migration in agarose gel 1% of the input vectors pENTR™ (VE) and the binary vectors pMDC162 (VB) containing the fragments PSulfT0.5, PSulfT0.8, PSulfT0.9. The enzymes used were EcoRV and NotI in the case of input vectors and XbaI in the case of binary vectors. M: 1 Kb plus DNA LADDER.

The colonies containing the pENTR™ vectors, where the putative promoter sequences were cloned, were inoculated in vials with 3 mL of LB medium (Sambrook and Russell, Molecular clone/ng–. A laboratory manual 3. New York: Cold Spring Harbor Laboratory Press, 2001) selective fluid (50 μg/mL kanamycin) and kept in an incubator for 16 hours with agitation at 200 rpm and 37° C. Aliquots of 1.5 mL were transferred to the microfuge tube and centrifuged for three minutes×13792 g (rcf). The supernatant was discarded and the remaining culture was added, i.e., 1.5 mL. After centrifugation and removal of supernatant, the precipitate was resuspended in 100 μL of TE (Tris-HCl 10 mM pH 8; EDTA 1 mM). Then, 200 μL of NaSE solution was added (NaOH 0.2 M; SDS 1%; EDTA 10 mM) and the tubes were shaken lightly. After five minutes at ambient temperature, 30 μL of KAc 5 M pH 4.8 was added. The samples were incubated for five minutes on ice and then centrifuged for five minutes at 13,400×g at 4° C. The supernatants were transferred to new tubes containing 2 μL of RNase A [10 mg/mL], and left for 20 minutes at 37° C. in a water bath. The solutions were then slowly homogenized with 450 μL of LiCl 5M, incubated for two hours at –20° C. and centrifuged for ten minutes at 13,400×g at 4° C. Again, the supernatants were transferred to new tubes containing half volume of isopropanol, left for five minutes at ambient temperature and subjected to centrifugation for 15 minutes at 13,792×g (rcf). The precipitates were washed with 400 μL ethanol 70% in centrifugation at 13,400×g at 4° C. for three minutes. After drying the material, the DNA was resuspended in 40 μL of deionized water. To confirm the cloning of DNA fragments, the plasmids were digested with the enzymes NotI and EcoRV (GIBCO BRL™) in a reaction of 20 μL containing 1× reaction buffer, three units of each enzyme and 5 μL of the DNA extracted from the input clones. The digestion took place for one hour at 37° C. in a water bath and was analyzed by electrophoresis in 1% agarose gel stained with ethidium bromide (FIG. 10).

The pENTR™ vectors containing the promoters PSulfT0.5, PSulfT0.8 PSulfT0.9 released, respectively, fragments of approximately 0.5 kb; 0.8 kb; and 0.9 kb (FIG. 10), as predicted for the digestion of vectors with NotI and EcoRV.

Example 9—Site-Specific Recombination

A site-specific recombination reaction was assembled so that the fragment of the input vector promoter region was transferred to the binary vector, or destination vector.

The destination vector used was the PMDC 162 (Curtis and Grossniklaus A Gateway Cloning Vector Set for High-Throughput Functional Analysis of Genes in Plant., Plant Physiology, v. 133, n. 2, p. 462-469, 2003) (FIG. 9), donated by the University of Zurich-Switzerland.

The reaction was assembled in a final volume of 8 μL with approximately 150 ng of input vector linearized with EcoRV and PvuII enzyme (GIBCO BRL™) (if the promoter region contains the recognition site of EcoRV), 150 ng of the destination vector pMDC162 and if necessary completed with TE buffer, pH 8. The components were briefly agitated and centrifuged and then 2 μL of Gateway® LR Clonase™ II Enzyme Mix (Invitrogen™) was added, in accordance with the manufacturer's protocol. Again the samples were briefly agitated and centrifuged. Then, the reactions were incubated for five hours at 25° C. To complete the reaction, 1 μL of proteinase K was added to the tube and the reaction was incubated for ten minutes at 37° C. The product of interest for this recombination reaction is the binary vector pMDC162 containing the promoter region upstream from the GUS gene.

To generate expression clones (cells transformed with the expression vector), the chemically competent cells were transformed by heat shock OmniMAX™ (Invitrogen™) with the product of the LR reaction. In a microfuge tube containing 100 μL of competent cells, 5 μL of the LR reaction was added and the mixture was incubated for 30 minutes on ice. After this period, the thermal shock was given for 90 seconds at 42° C. and 500 μL of SOC medium (Sambrook and Russell, Molecular Cloning—A laboratory manual 3. New York: Cold Spring Harbor Laboratory Press, 2001.) was added. The culture was incubated for one hour at 37° C. The cells were then precipitated by centrifugation at 13,792×g for 1 minute, part of the supernatant medium was discarded and the cells were resuspended in remaining medium (≈100 μL). The cells were spread on Petri dishes with LB medium-solid (Sambrook and Russell, Molecular Cloning—A laboratory manual 3. New York: Cold Spring Harbor Laboratory Press, 2001) and kanamycin [50 μg/mL] and incubated at 37° C. for 14 hours. Resistant colonies were inoculated in 3 mL of LB medium for plasmid isolation according to the protocol described above. The expression vector (destination vector pMDC162 containing the different fragments of the promoter region), in turn, was digested with the enzyme XbaI in 30 μl of reaction with 1× reaction buffer, 20 units of enzyme and 20 μL of the vectors pMDC162. Just as the input vector, the digestions of the PMDC 62 occurred for one hour at 37° C. and were analyzed by electrophoresis in 1% agarose gel stained with ethidium bromide (FIG. 10). The restriction of the binary vectors, resulting from the LR recombination reaction with the enzyme XbaI generated fragments corresponding to the putative promoters PSulfT0.5, PSulfT0.8 and PSulfT0.9 (FIG. 10).

Example 10—Transformation of *Agrobacterium tumefaciens*

The binary plasmids extracted from the positive clones were inserted into competent cells of *Agrobacterium tumefaciens* strain GV3101 by electroporation. In a microfuge tube containing 40 μL of cells, 1 μL (50-300 ng/μL) of plasmid was added and the mixture transferred to a 0.2 cm cuvette. Then the cells were subjected to an electrical pulse of 25 μF, 2.5 kV, 200Ω, 5.5 seconds and then immediately 1 mL of SOC medium (Sambrook and Russell, Molecular Cloning—A laboratory manual 3. New York: Cold Spring Harbor Laboratory Press, 2001) was added to the electroporation cuvette. The culture was transferred to a new microfuge tube and incubated for 60 minutes at 28° C. for the cells to recover their membrane. After this period, 30 and 100 μL of culture was spread on two Petri dishes containing LB agar medium (Sambrook and Russell, Molecular Cloning—A laboratory manual 3. New York: Cold Spring Harbor Laboratory Press, 2001) with kanamycin [100 μL/ml], gentamicin [50 μL/mL] and rifampicin [100 μg/ml] and incubated for approximately 48 hours at 28° C.

Example 11—Validation In Vivo: Transformation of *Nicotiana tabacum* Plants

The transformation of *Nicotiana tabacum* was made according to Barros (BARROS, L. M. G. Genetic transformation of *Nicotiana tabacum* cv Xanthi using *Agrobacterium tumefaciens* and electroporation. Master's Thesis. University of Brasilia, DF, Brazil, 177p, 1989), with modifications.

The colonies containing the binary vectors pMDC 162 containing the putative promoter regions upstream of the GUS gene were inoculated in 5 mL of LB medium (Sambrook and Russell, Molecular Cloning—A laboratory manual 3. New York: Cold Spring Harbor Laboratory Press, 2001), kanamycin [100 μg/ml] gentamicin [50 μg/mL] and rifampicin [100 μg/ml] and incubated at 180 rpm for approximately 24 hours at 28° C. Fifty microliters of this pre-inoculum were placed into 50 ml of LB medium and again incubated at 180 rpm for approximately 15 hours at 28° C.

Young leaves (third from the apex) of *Nicotiana tabacum* plants were collected from plants with 55 and 80 days cultivated in a greenhouse and immediately placed in water. In chapel vertical laminar flow, the leaves were washed with 1 liter of ethanol 50% and then sterilized with sodium hypochlorite solution of 2% for 20 minutes. After this period the leaves were washed three times in sterile Milli-Q water and kept in a beaker of sterile water while they were not handled.

In parallel, the bacterial culture containing the binary vector pMDC162+PSulfT0.5 was distributed in two Petri dishes and left in the chapel. In a Petri dish of 130 mm×15 mm containing sterile filter paper, the leaf was divided in half, the midrib and the edges were withdrawn with the assistance of a scalpel blade and then the rest was cut into squares of 0.6×0.6 cm approx. As they were cut, the explants were submerged in the culture of *A. tumefaciens* until the entire surface of the two Petri dishes of 90 mm×15 mm containing the bacterial culture was covered with leaf explants. The negative controls were dipped in LB medium without bacteria. Then the explants were transferred to filter paper to remove excess bacteria, and placed on Petri dishes of 90 mm×15 mm containing MS medium (SIGMA) (Murashige and Skoog, A revised medium for rapid growth and bioassays with tobacco tissue cultures. Physologia Plantarum, vol. 15, p. 473-497, 1962) pH 5.6-5.8 with 3% sucrose, 6-benzylaminopurine (Sigma) (1 mg/mL) and agar (purified tissue culture—SIGMA) 0.3%, with the adaxial surface facing the medium. The plates were sealed with plastic wrap and placed in a culture heated room (28° C.) in the dark for two days.

The expression vector used for tobacco transformation include the hpt gene whose product, the protein hygromycin phosphotransferase, confers the plant resistance to hygromycin. Thus, after co-culture of two days for selecting transformed explants and eliminating the agrobacteria, the explants were transferred to Petri dishes containing MS medium (SIGMA) (Murashige and Skoog, A revised medium for rapid growth and bioassays with tobacco tissue cultures. Physologia Plantarum, vol. 15, p. 473-497, 1962) pH 5.6-5.8 with 3% sucrose, 6-benzylaminopurine (Sigma) (1 mg/mL) and 0.3% agar, cefotaxime added [500 μL/ml] and hygromycin [200 μL/mL]. The plates were sealed with plastic film and incubated in an acclimatized culture room (28° C.) under controlled photoperiod of 16 hours light and eight hours of dark. Hygromycin was not added to the plates with negative controls. Every two weeks, a period that antibiotics are beginning to wear off, the explants were transferred to new plates.

One month after transfer to the selective medium, the regenerated and transformed shoots were transferred to test tubes with MS medium (SIGMA) (Murashige and Skoog, A revised medium for rapid growth and bioassays with tobacco tissue cultures. Physologia Plantarum, v. 15, pp 473-497, 1962), pH 5.6-5.8; 2% sucrose; 0.3% agar containing cefotaxime [300 μg/mL] and hygromycin [200 μg/mL]. The tubes with the shoots were sealed and incubated in the culture room under the same conditions as above. The non-transformed shoots (negative control) were transferred to tubes containing the same culture medium used for the transformed shoots, but without the addition of antibiotics.

The plants that rooted in the test tubes were transferred to small bags with wet and chemically fertilized land. After washing the root with water to remove the culture medium, the plant was placed in soil and covered with a transparent plastic bag. During this stage, root and leaf segments were collected for carrying out a histochemical test for detecting GUS reporter enzyme activity. The plants were kept in a greenhouse with temperature and natural photoperiod. The transparent plastic bags were opened at the ends progressively from the first week to allow the plants to acclimatize gradually to the conditions of the greenhouse and after two weeks the bags were completely removed.

To characterize the activity of the fragments of the promoters through regulating the expression of the GUS reporter gene, a histochemical assay was performed in accordance with McCabe, 988 (Stable transformation of soybean (*Glycine max*) by particle acceleration. Biotechnology, vol. 6, p. 923-926, 1988). The segments of the root tips and leaves collected during the transfer of the plants from the test tube to soil were incubated in a solution containing the substrate X-Gluc (5-bromo-4-chloro-3-indolyl-β-D glucuronide) at a concentration of 2 mM, that is: 100 mg X-Gluc was dissolved in 2 mL of DMSO and added to a solution containing 10 mM EDTA, 100 mM NaH2PO4, K4Fe(CN)6 3H2O 0.5 mM, Triton X-100 0.1%, ascorbic acid 1% and water to make up 200 mL. The final pH of the solution was adjusted to pH 7.0 with NaOH 10 M and the solution finally filtered through a Millex® sterile filter (Millipore membrane with pore μM 45) and stored at −20° C. The segments of the roots and leaves were placed in wells of ELISA plates containing 200 μL solution and incubated in an incubator at 37° C. for 18 hours. After this period the solution was removed with the aid of an automatic pipette and 70% ethanol was added to remove the chlorophyll and better visualize the end of the reaction product, indigo blue. The ethanol was changed several times until the chlorophyll was completely removed. The test result was displayed on the magnifying glass SteREO Discovery.V8 (Zeiss) and the images captured (FIG. 11/FIG. 14).

Figure 11:
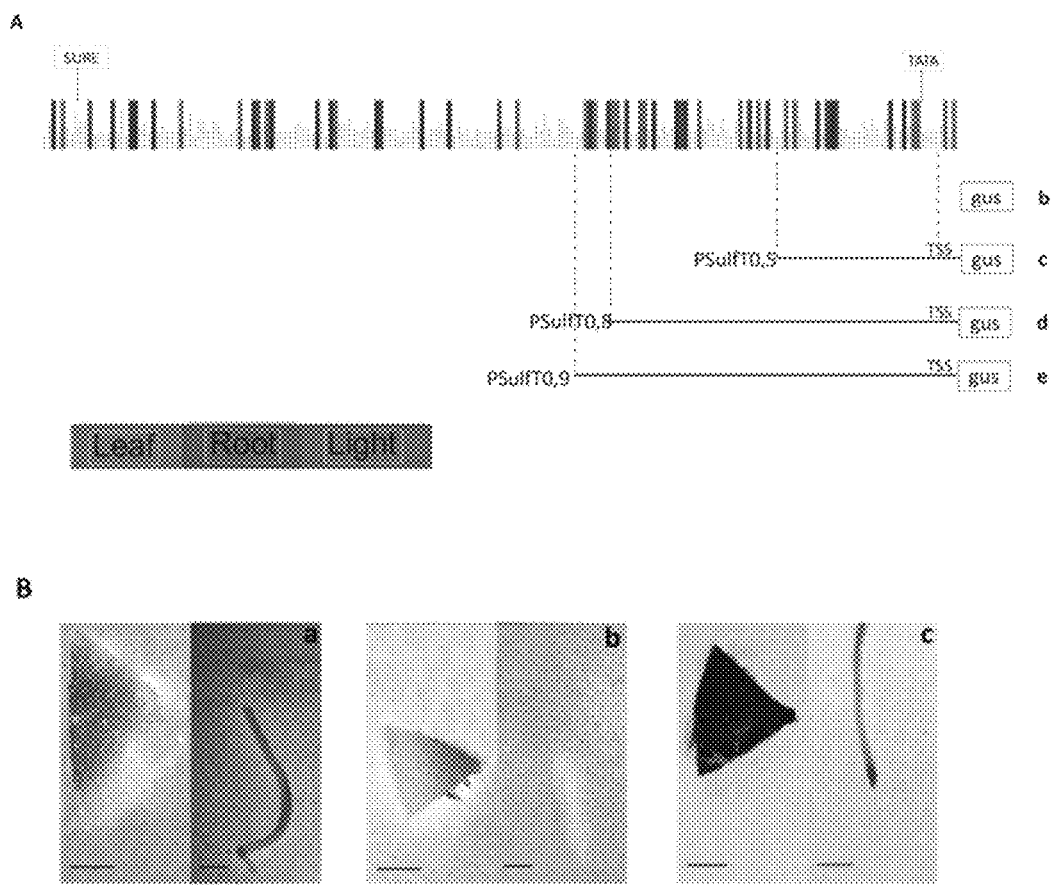
FIG. 11/FIG. 14. In silico and functional analysis of the promoter region of GmSulfT1. (A) representation of the putative motives of the cis elements found in the promoter region (sense strand) with 1.8 kb. The upper bar shows the TATA Box and the sulfur-responsive element Sure (SURECOREATSULTR11). The highlighted elements needed for organ-specific expression are: OSE1 ROOTNODULE, OSE2ROOTNODULE and ROOTMOTIFTAPDX1 and RHERPATEXPA7 responsible for gene expression in root, CACTFTPPCA1 and TAAGSTKST1 needed for expression in leaf and ACGTOSGLUB1, SEF1 MOTIF and SEF4MOTIFGM7S related to seed-specific expression. In the lower part b represents the promoterless GUS gene and c represents the GUS gene with the promoter PSulfT0.5 and (B) histochemical assay on leaf (left) and root (right) of the non-transformed plant (a) of the transformed plant with the promoterless binary vector (b) and in leaf (left) and root (right), seed and pollen (indicated by the arrow), petal, stamen and carpel (stigma to the left and ovary to the right), left to right, respectively, of the tobacco plants of the transformed with the binary vector containing the promoter PSulfT0.5 (c). The bar at the bottom of the photos corresponds to 1 mm in a and b and 0.5 mm in c.
Figure 12:
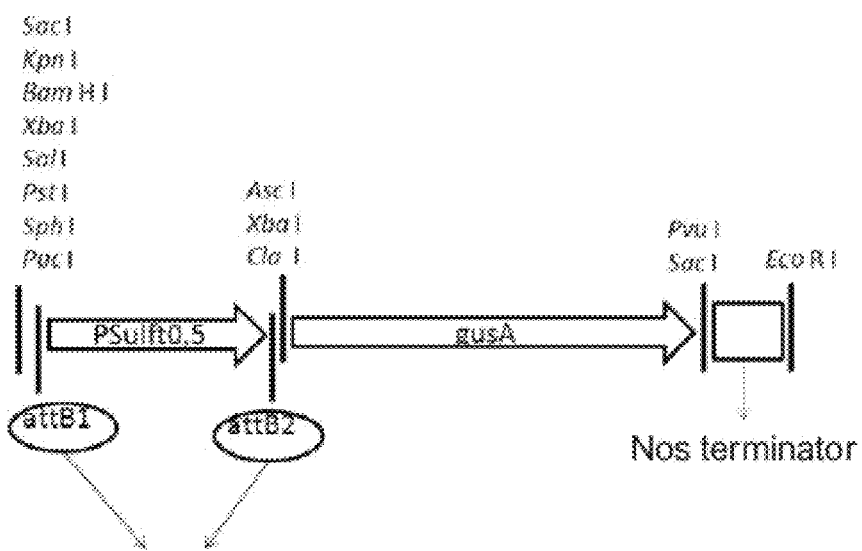
FIG. 12: Expression cassette containing the promoter PSulfT0.5.
Figure 13:
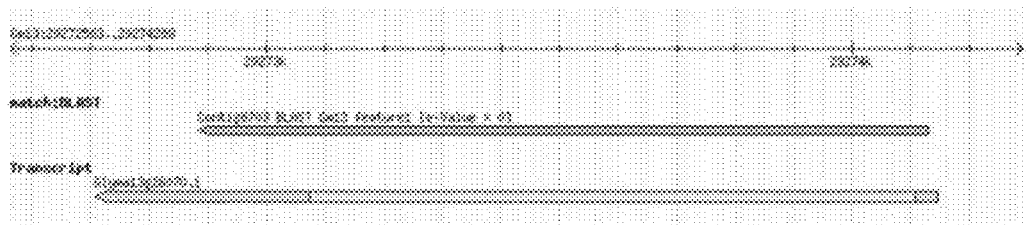
FIG. 13. Comparative analysis of the sequence of contig 8703, 1043 pb, with the soybean genome in the Phytozome (www.phytozome.net/). The Glyma13g26070.1 transcript of the chromosome Gm13 that aligned with the contig 8703 (in blue) being 100% identical is indicated in yellow.
Figure 14:
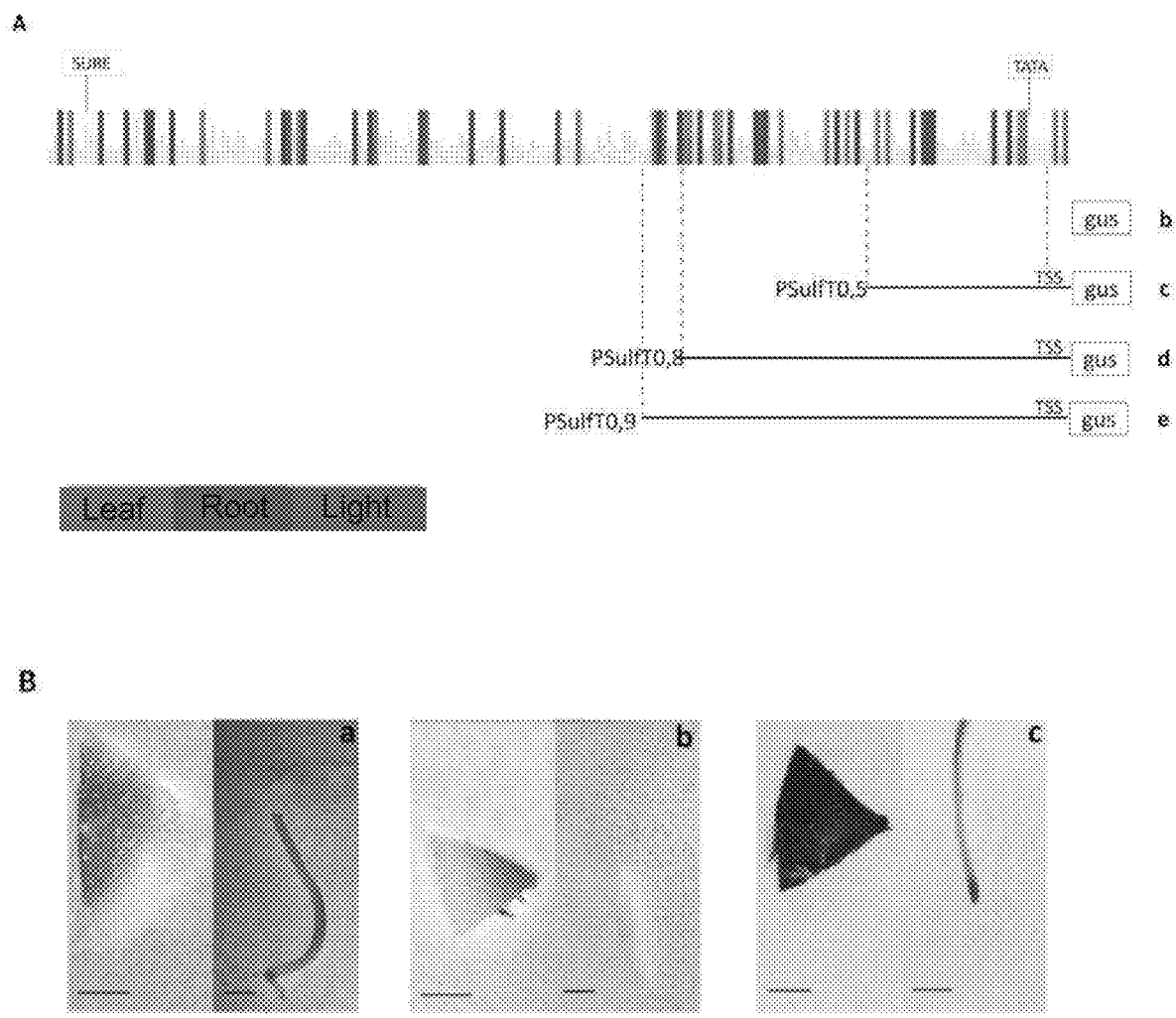

Promoters generated from deletions 5' of the promoter region of GmSulfT1 are represented with their putative motifs of cis elements in FIG. 11-A/FIG. 14. FIG. 11 B/FIG. 14 shows the histochemical assay on leaf and root tobacco plant leaf and root, untransformed and transformed with the promoterless binary vector, and on tobacco plant leaf, root, seed and pollen, petal, stamen and carpel transformed with the PSulfT0.5 promoter. It is noted that the PSulfT0.5, promoter of the present invention (SEQ ID NO: 1) was able to activate the expression in all organs of plants analyzed, and this expression was stronger in leaf, root and seed. FIG. 12 shows the expression cassette used in the present invention.

---

The invention claimed is:

1. A nucleic acid molecule, wherein said nucleic acid molecule comprises a polynucleotide sequence having at least 95% sequence identity to the nucleotide sequence of SEQ ID NO: 1, linked to a nucleotide sequence that is heterologous with respect to SEQ ID NO: 1, wherein said polynucleotide sequence has promoter activity.

2. The nucleic acid molecule according to claim 1, wherein said nucleic acid molecule further comprises one or more expression-enhancing sequences.

3. The nucleic acid molecule according to claim 1, wherein said nucleotide sequence heterologous to SEQ ID NO: 1 comprises a coding region encoding a protein of interest.

4. The nucleic acid molecule according to claim 3, wherein said coding region is exogenous with respect to SEQ ID NO: 1.

5. The nucleic acid molecule according to claim 1, wherein the nucleotide sequence that is heterologous with respect to SEQ ID NO: 1 is a polynucleotide sequence of interest in sense or antisense orientation.

6. The nucleic acid molecule according to claim 2, wherein the one or more expression-enhancing sequences are from a virus selected from the group consisting of SV40, HSV-1, Alfalfa Mosaic Virus (AMV) and HPV-16.

7. A recombinant vector comprising the nucleic acid molecule according to claim 1.

8. The recombinant vector according to claim 7, wherein said recombinant vector further comprises one or more expression-enhancing sequences and at least one termination sequence.

9. The recombinant vector according to claim 8, wherein the nucleotide sequence heterologous to SEQ ID NO: 1 comprises a coding region encoding a protein of interest.

10. The recombinant vector according to claim 9, wherein the coding region is exogenous with respect to SEQ ID NO: 1.

11. The recombinant vector according to claim 8, wherein said vector comprises a termination sequence selected from the group consisting of SV40 termination signal, HSV TK adenylation signal, termination signal of the nopaline synthase gene of *Agrobacterium tumefaciens*, termination signal of the octopine synthase gene, terminal signal of the gene 19S and 35S of CaMV, termination signal of the alcohol dehydrogenase gene from maize, termination signal of the mannopine synthase gene, termination signal of the beta-phaseolin gene, termination signal of the ssRUBISCO gene, termination signal of the sucrose synthase gene, termination signal of Subterranean clover stunt virus (SCSV), and termination signal of the trpC gene of *Aspergillus nidulans*.

12. The recombinant vector according to claim 8, wherein the one or more expression-enhancing sequences are from a virus selected from the group consisting of SV40, HSV-1, AMV and HPV-16.

13. A transformed cell, wherein said transformed cell comprises the recombinant vector according to claim 7.

14. A plant, or a part, or a propagule or progeny thereof, which comprises the recombinant vector according to claim 7.

15. A method for expressing a protein of interest in an organism, said method comprising stabling incorporating into the genome of the organism the recombinant vector according to claim 9.

16. The method according to claim 15, wherein said organism is a plant.

17. A method for producing a plant expressing a protein of interest, said method comprising:
 a) transforming a plant cell, tissue, organ or embryo with the recombinant vector according to claim 9;
 b) selecting cells, cell callus, embryos or seeds transformed with said recombinant vector;
 c) producing mature plants from the transformed cells, cell callus, embryos or seeds selected in step (b); and
 d) selecting mature plants from step (c) expressing the protein of interest.

18. A method for expressing a protein of interest in an organism, said method comprising stabling incorporating into the genome of the organism the nucleic acid molecule according to claim 3.

19. A method for producing a plant expressing a protein of interest, said method comprising:
 a) transforming a plant cell, tissue, organ, or embryo with the nucleic acid molecule according to claim 3;
 b) selecting cells, cell callus, embryos or seeds transformed with said nucleic acid molecule;
 c) producing mature plants from the transformed cells, cell callus, embryos or seeds selected in step (b); and
 d) selecting mature plants from step (c) expressing the protein of interest.

* * * * *